US010421002B2

(12) United States Patent
Smith

(10) Patent No.: US 10,421,002 B2
(45) Date of Patent: *Sep. 24, 2019

(54) EQUIPMENT, SYSTEM AND METHOD FOR IMPROVING EXERCISE EFFICIENCY IN A CARDIO-FITNESS MACHINE

(71) Applicant: Kelly Ann Smith, Katonah, NY (US)

(72) Inventor: Kelly Ann Smith, Katonah, NY (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/278,973

(22) Filed: Sep. 28, 2016

(65) Prior Publication Data

US 2017/0080320 A1 Mar. 23, 2017

Related U.S. Application Data

(63) Continuation-in-part of application No. 13/792,658, filed on Mar. 11, 2013, now Pat. No. 9,460,700.

(51) Int. Cl.
*A63B 71/06* (2006.01)
*G10H 1/42* (2006.01)
(Continued)

(52) U.S. Cl.
CPC ........ *A63B 71/0622* (2013.01); *A63F 13/245* (2014.09); *A63F 13/44* (2014.09); *G10H 1/40* (2013.01); *G10H 1/42* (2013.01); *G16H 20/30* (2018.01); *G16H 40/67* (2018.01); *A63B 21/0051* (2013.01); *A63B 21/225* (2013.01); *A63B 22/02* (2013.01); *A63B 22/0605* (2013.01); *A63B 22/0664* (2013.01); *A63B 24/0075* (2013.01); *A63B 24/0087* (2013.01); *A63B 2022/067* (2013.01); *A63B 2022/0682* (2013.01); *A63B 2024/0012* (2013.01); *A63B 2024/0015* (2013.01); *A63B 2071/0625* (2013.01); *A63B 2071/0638* (2013.01);
(Continued)

(58) Field of Classification Search
None
See application file for complete search history.

(56) References Cited

U.S. PATENT DOCUMENTS 6,227,968 B1 * 5/2001 Suzuki .................... A63F 13/08 463/7
2008/0201639 A1 * 8/2008 Shoman ............ A63B 71/0622 715/716

(Continued)

*Primary Examiner* — Sundhara M Ganesan

(57) ABSTRACT

A system, equipment and process to guide a user in the experience of rhythmic exercise. Playback of an audio file/signal, such as a musical phrase, that has known rhythmic structure (e.g., beat pattern) is accompanied, by non-audio sensory cues such as a light signal or tactical signal (vibration) to mark rhythmic events in the audio playback (such as the beginning and end of playback and/or audio pulses (beats). In addition, equipment is provided to guide the user in performing a GDM (goal directed movement) sequence that is selected to be performed in synch with the rhythm of the audio signal. The user's motion is detected and compared to desired GDM in the selected sequence and also compared to the rhythm of the audio signal. Sensory cues are provided to guide the user in performing the GDM sequence rhythmically. The system may be implemented in cardio fitness equipment including treadmill, AMT, stationary exercise bike and elliptical type exercise equipment.

17 Claims, 14 Drawing Sheets

(51) Int. Cl.

| | |
|---|---|
| ***G10H 1/40*** | (2006.01) |
| ***A63F 13/245*** | (2014.01) |
| ***A63F 13/44*** | (2014.01) |
| ***G16H 40/67*** | (2018.01) |
| ***G16H 20/30*** | (2018.01) |
| ***A63B 22/06*** | (2006.01) |
| *G06F 3/16* | (2006.01) |
| *A63B 22/02* | (2006.01) |
| *A63B 24/00* | (2006.01) |
| *H04M 1/725* | (2006.01) |
| *G02B 27/01* | (2006.01) |
| *A63B 21/005* | (2006.01) |
| *A63B 21/22* | (2006.01) |

(52) U.S. Cl.

CPC ................. *A63B 2071/0655* (2013.01); *A63B 2071/0694* (2013.01); *A63B 2207/02* (2013.01); *A63B 2220/36* (2013.01); *A63B 2220/40* (2013.01); *A63B 2220/51* (2013.01); *A63B 2220/52* (2013.01); *A63B 2220/53* (2013.01); *A63B 2220/803* (2013.01); *A63B 2220/805* (2013.01); *A63B 2220/806* (2013.01); *A63B 2220/833* (2013.01); *A63B 2220/836* (2013.01); *A63B 2225/20* (2013.01); *A63B 2225/50* (2013.01); *A63F 2300/8047* (2013.01); *G02B 27/017* (2013.01); *G06F 3/165* (2013.01); *G10H 2210/076* (2013.01); *G10H 2220/341* (2013.01); *G10H 2220/371* (2013.01); *G10H 2220/421* (2013.01); *G10H 2230/015* (2013.01); *H04M 1/7253* (2013.01)

(56) References Cited

U.S. PATENT DOCUMENTS

| | | | | |
|---|---|---|---|---|
| 2012/0021873 A1* | 1/2012 | Brunner | ............. | A63B 22/0235 482/9 |
| 2014/0228173 A1* | 8/2014 | Shaw | ................. | A63B 71/0622 482/4 |

* cited by examiner

EQUIPMENT, SYSTEM AND METHOD FOR IMPROVING EXERCISE EFFICIENCY IN A CARDIO-FITNESS MACHINE

CROSS-REFERENCE TO RELATED APPLICATION

This application is a continuation-in-part of and claims the benefit under 35 U.S.C. § 120 of applicant's earlier U.S. patent application Ser. No. 13/792,658, filed Mar. 11, 2013, now U.S. Pat. No. 9,460,700 issued on Sep. 11, 2016.

BACKGROUND

1. Technical Field

The present invention relates to a system and method of improved exercise through rhythmic cuing using sensors for detecting left and right initiated goal directed movement sequences on a foot platform of a cardio-fitness machine, or while seated on an exercise bike and a musical phrase having a grouping of beats whereby sound signals in the musical phrase coincide with light emissions that guide the users movement to be detected.

2. Description of the Related Art

Some games use rhythmic motion to advance the process of a game. Rhythmic motion is also used to rehabilitate those with movement impairment. Rhythmic exercise is currently popular in indoor cycling to music or floor exercises performed in groups settings. Visual sensory stimuli are most commonly used in the performance of these rhythmic tasks. Either a leader or an instructor of some sort guide participants to base their movements on visuals to perform the exercise correctly in time with music. In other forms of conventional exercise, music combines with movement for motivational and distractive purposes only. Popular running and biking activities that use music to exercise to lack the precision movement that develops rhythmic sensorimotor skill. And gesture based gaming exercise known as exergames opt the user to synchronize motion with moving images—not the music per se. As a result exergaming fails to offer participants a system and method for assimilating rhythmic feedback to guide future performances more precisely during exercise. Using goal directed movement patterns on cardio-fitness machines addresses these issues and creates a new form of exercise that stimulates a discovery of sensorimotor acuity beneficial to overall human health.

Recent improvements and cost reductions in contactless movement sensing have brought such technology within reach of consumer products such as video games. 3-D perception is accomplished through devices that sense depth and collect 3-D information in raw form as a collection of points (point cloud) that represents the 3-D space or object. There are various approaches to capturing such information, but the two most accurate are time of light and structured light sensing.

Time of flight sensing involves pulsing infrared light or lasers (invisible to the eye) at the object, measuring the time it takes for the light to return, and computing the distance. The system acquires a 3-D equivalent of an image bitmap, where the collection of points approximates the object. To reduce processing and bandwidth demands an approach known as motion contrast may be used—rescanning only the areas where visual changes are detected. This approach is analogous to video compression techniques, where a video is compressed by storing only the visual changes, thereby requiring less storage and bandwidth.

The structured light approach projects an infrared pattern (invisible to the eye), photographs the pattern through a separate camera, and then calculates distances and angles from the distortions of the pattern. This method provides the appropriate balance of cost and accuracy and can also be packaged in small form factors. One of the first consumer products to use structured light was the Microsoft Kinect sensor for Xbox gaming applications.

Thibaut Weise, Bastian Leibe and Luc Van Gool of the Swiss Federal Institute of Technology (ETH Zurich) have described a 3D scanning system combining stereo and active illumination based on phase-shift for robust and accurate scene reconstruction. Due to the sequential recording of three patterns, motion will introduce artifacts in the reconstruction. A closed-form expression for the motion error is used in order to apply motion compensation on a pixel level. The resulting scanning system can capture accurate depth maps of complex dynamic scenes at 17 fps and can cope with both rigid and deformable objects. Motion Contrast 3D scanning maximizes bandwidth and light source power to avoid performance trade-offs. This technique allows laser scanning resolution with single-shot speed, even in the presence of strong ambient illumination, significant interreflections, and highly reflective surfaces. State of the art movement sensors may be used in conjunction with virtual or augmented reality headsets (e.g., Oculus Rift, HTC Vive) to allow users to experience an immersive virtual or augmented reality.

SUMMARY

To enable users to experience auditory cues for rhythmic exercise, a motion sensor system and method of rhythmic cuing to perform goal directed movement sequences on a cardio-fitness machine is novel and useful to furthering what is therapeutic and conventional in rhythmic exercise. Recent research has shown that in NMT—neurological music therapy, professionals rehabilitate the movement impaired primarily using the auditory pathways in structured rhythmic tasks that increasingly meet greater performance objectives. The present inventor recognizes that the auditory pathways strengthen rhythmic skills more so than the visual pathways. Auditory stimuli therefore have a greater potential to enhance performance of rhythmic tasks of all sorts including those tasks that combine upper body movement or movement with the arms while moving the feet on a foot platform or with foot platforms.

The object of the present invention of a motion sensor system and method of rhythmic cuing for sensorimotor synchronizing of audible pulses (beats) corresponding to visible cues to guide the users actions to be detected comprises: sensors for detecting a plurality of distinct goal directed movement sequences including an initial GDM at the initiation of the GDM sequence and a final GDM at the completion of the GDM Sequence on a foot platform of a cardio-fitness machine, either while seated or in a standing position, and a musical phrase having a grouping of beats whereby sound signals in a musical phrase or a collection of musical phrases such as that composing a song coincide with light emissions that guide the users movement to be detected.

Exercise as used herein involves goal directed movement of a user's limbs (i.e., left foot, right foot, left arm, right arm). In some instances, an exercise is focused on goal directed movement of the legs, in others the exercise is focused on goal directed movement of the arms, and some exercise involves goal directed movement of all four limbs (arms and legs). Cardio fitness machines typically provide needed support for a user's feet, but a user's upper limbs (arms) are typically unsupported, though hand grips or handles may be provided. As such the path of movement of the upper limbs may not be as reliably restrained as the lower limbs. Nonetheless, the movement of upper limbs can be sensed using time of flight and similar contactless movement sensing equipment.

Sensing movement of upper limbs can facilitate additional forms of exercise. When a user is seated on a stationary bike, for example, the customary placement of user's hands is on the handle bar and the lower limbs are customarily placed so that the user's right foot is on a right foot platform (pedal) and the left foot on the left foot platform (pedal). In a stationary bike having a control panel and contactless motion sensing equipment however goal directed movement of the user's arms may be facilitated as follows.

With this system and method, movement of the user is detected in an exercise space associated with a right side of the user and an exercise space of the left side of the user in laterally opposite sections of the exercise space provided by a foot platform of a cardio-fitness machine as well as in the exercise space within a substantially known spatial area of the upper body relative to either a right side movement or a left side movement and a sequence involving those movements. A right limb (e.g., foot and/or arm) movement is detected by a right sensor having a detection range for detecting right side movement, for example, in a lateral section of a cardio-fitness machine's foot platform, and a left limb (foot and/or arm) movement is detected by a left sensor having a suitable detection range in a section of the exercise space laterally opposite the detection range of the right sensor. Right side movements and left side movements on and with the foot platform(s) may also be detected by a respective tactile sensor located within the foot platform or may be detected from an alternate location such as the user's shoe.

A method of improving exercise efficiency by facilitating rhythmic exercise through coordinating goal directed movement in a goal directed movement sequence with beat pulses in an audio file; The method comprising the steps of selecting an audio file, determining the timing and location of beat pulses in the user selected audio file and selecting a goal directed movement (GDM) sequence and identifying the plurality of distinct GDMs including a sequence of right limb movements and left limb movements in the user selected GDM sequence. The method further comprises the steps of generating a non-audio (e.g., visual or tactile) sensory cue at the initiation and conclusion of the user selected audio file playback and a second sensory cue generating a sensory cue at the initiation and conclusion of the user selected GDM sequence. During audio file playback, a control panel is configured to load stored audio file data in response to the user's selection of the audio file and load stored GDM sequence data in response to the user selection of the GDM sequence. The timing of performance of the selected GDM sequence is then compared with timing of beat pulses in the selected audio file to provide the user with feedback. The step of comparing the timing of performance of GDM sequence with timing of beat pulses in the audio file includes the step of storing separate counts of the left limb movements and the right limb movements and comparing them to a number of pulses in the user selected audio file.

The timing and location of the beat pulses in the user selected audio file is determined by reading data (stored locally or on a network) or using a beat detection engine to extract beat data from the digital music file. A beat detection engine with multiple beat detectors operating simultaneously to extract beat data from a digital music file may be used to provide a multi-faceted rhythm map.

A plurality of motion sensors may be used to detect the user GDM associated with the user selected GDM sequence. At least one left sensor and one right sensor may be used so that motion in an exercise space associated with a right side of the user may be distinguished from motion associated with a left side of the user. In addition, or alternatively, a time of flight sensing system (such as that now used in video gaming systems, for example) may be used to detect the user GDM associated with the user selected GDM sequence. In addition, or alternatively, a plurality of wireless sensors worn by the user (foot wear, athletic apparel or bands) may be used to detect user GDM associated with the GDM sequence. The method may also include the step of detecting foot pressure applied to a foot platform of the cardio fitness machine. Foot pressure data may be useful to determine whether the foot movement signal received is the first movement signal of the user selected GDM sequence and, if so, flag the GDM sequence according to whether the limb movement was a left limb movement or a right limb movement.

The method may include a step of operating in expert mode whereby the control panel includes memory for storing data including storing audio file data and storing GDM sequence data in a new GDM sequence in either upper or lower body exercise space associated with right side movements and left side movements.

The invention may be implemented in cardio fitness machines i.e. stationary exercise bike that generate sensory cues to guide a user in performing GDM in a GDM sequence in coordination with playback of an audio file. Such machines include at least one movable foot support (in the case of a treadmill) or two moveable foot support platforms (in the case of an elliptical or exercise bike, for example) that comprise pedals that are constrained to move in a circular path and offset 180 degrees with respect to one another. A sensor system provides signals that allow the control system to distinguish between only movements in an exercise space associated with a left side of the user and only movements in an exercise space associated with a right side of the user, and as such, in a substantially known spatial area of the user's exercise space that would also include the exercise space associated with the user's upper limbs. A control system is configured to determine signals indicative of the user's movement and compares the movement pattern to a stored movement pattern.

The control panel further includes a beat detection engine configured to extract beat data from the user selected audio file; A plurality of sensory cue generators controlled independently of one another and configured such that a first sensory cue generator generates non-audio cue at the initiation and conclusion of the user selected audio file playback and another independent sensory cue is generated at the conclusion of the GDM sequence. The sensor system may include a plurality of motion sensors arranged to detect the user GDM associated with the selected user GDM sequence, at least one of the motion sensors positioned to detect only motion in an exercise space associated with a left side of a user, and at least one of the motion sensors positioned to detect only motion in an exercise space associated with a right side of a user, i.e. usually the legs and feet, but also able to distinguish arm and hand movement. The system may also include a plurality of pressure sensors arranged to detect pressure applied by a user's foot to a foot platform of the machine, or a hand to a handle bar of the machine (or exercise bike for example) the pressure sensors providing signals to allow the control system to distinguish between right and left foot pressure or right and left hand pressure.

The invention may also be implemented as a system for generating sensory cues to guide a user in performing GDM in a user selected GDM sequence, i.e. with the lower limbs simultaneously moving with upper limbs, in coordination with rhythmic elements of an audio file during playback. The system may be configured to receive signals from right and left sensors indicative of a sequence of detected movements in the exercise space associated with the right and left side of the user in addition to receiving signals from right and left sensors indicative of a sequence of detected movements associated with the right and left side of the user in a specific zone of movement including a first zone of movement associated with left arm movements and a second zone of movement associated with right arm movements. The system includes an audio playback system for playing an audio file having known beat characteristics. The system further includes a non-audio cue generator for generating a first non-audio cue (such as the flash of a light) to correspond with select beat pulses in the audio file. The select beat pulses may be the first and last beats in a musical phrase or, alternatively, some or all of the beats perceived during playback of the audio file. The audio file may comprise a single musical phrase or a more complex musical structure such a song. The system may include an expert mode engine to use the system equipment to store a user's new GDM sequence data as detected by the sensor system during audio file playback. The system may include additional sensory cue generators to, for example, generate additional sensory cues at the initiation and conclusion of a GDM sequence or in an instance where a GDM is detected. The system is preferably run by software operating on a general purpose computer that may include special purpose processors. Various software implemented engines may be used to process inputs from system components, the software implemented engines may include a beat data extraction engine, a laser light beam control engine, a gesture recognition engine, a performance assessment engine, a GDM preference engine, an expert mode engine, a MPORG engine, an audio encode, an audio decoder and a recommendation engine, and those others providing either a virtual reality experience or brain scan to further guide a user according to the system and method.

Open source technology in EEG and ECG biosensors promotes insight to how exercise benefits the brain but can do more. It can show how music impacts executive function of motor skills in the presence of minimal visual stimuli. Biometric algorithms are currently available to provide users with physiological feedback during and after a workout. However, by combining aural and proprioceptive learning modalities in musical exercise, additional sensory feedback, as a result of entrainment, could become measurable. Because learning of rhythmic patterns enables information to be stored in several areas of the brain, the brain can develop more memory pathways for retrieval of information. By listening to the same musical segment while performing a same rhythmic pattern, the repetitious retrieval focuses attention on making the effort to match the movement sequence with the beat events. In this way the combination of music and exercise changes people's perception of their efforts throughout a workout. Music may compete with physiological feedback for the brain's conscious attention. In other words users may not be as focused on heart rate or endurance stress. A user might be more concerned with keeping pace with the music according to a rhythmic objective.

These and other objects, features and advantages of the present invention will become more apparent upon reading of the following detailed description to the system and methods within the design.

DETAILED DESCRIPTION

Figure 1:
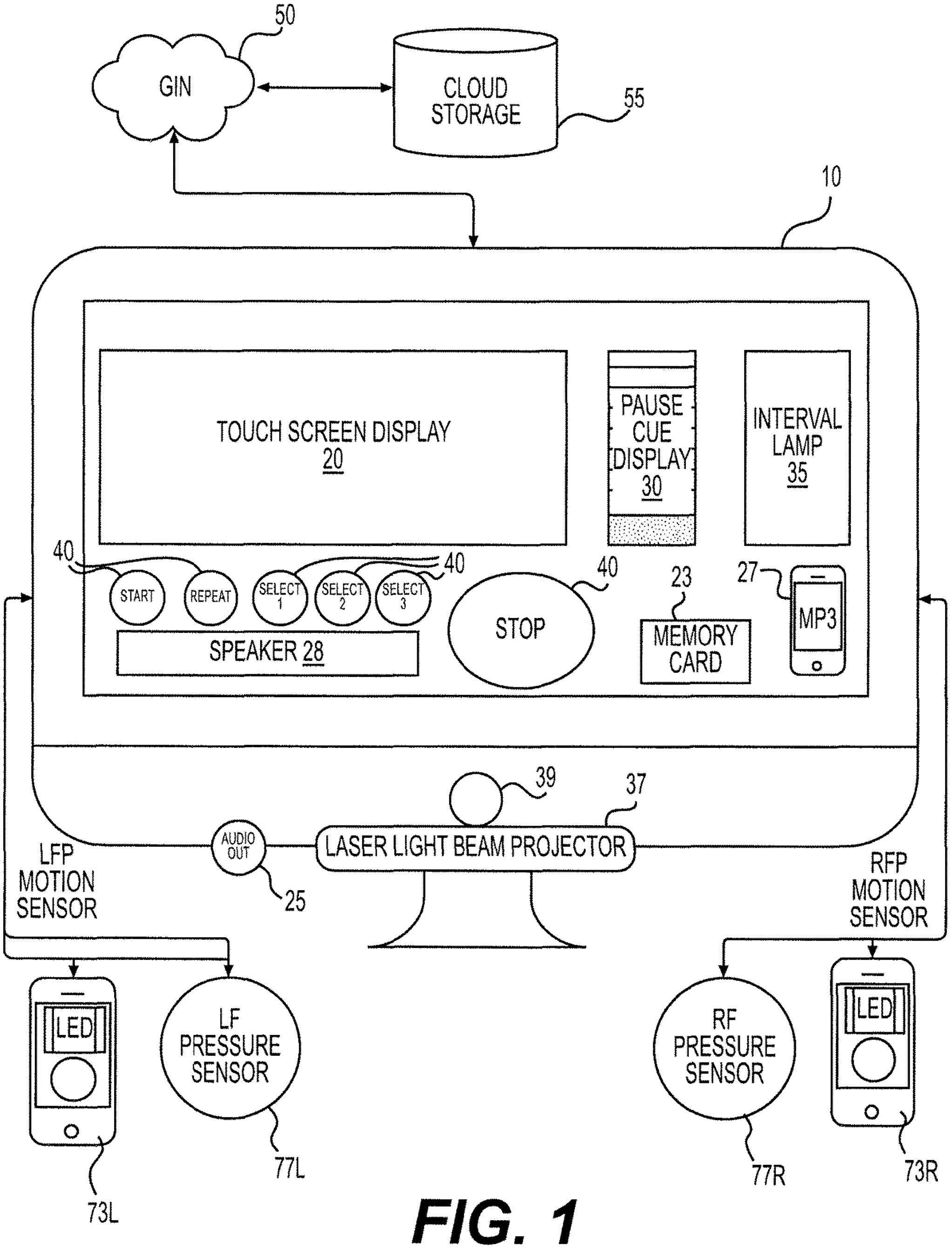
FIG. 1 is a schematic representation of the Control Panel and related hardware of an embodiment of the invention.

FIG. 1 is a schematic representation of the Control Panel 10 and related hardware of an embodiment of the invention. As shown, the Control Panel 10 includes a multi-touch screen display 20, a speaker 28, a pause cue display 30, an interval lamp 35, a laser light beam projector 37, and various user input selection buttons 40 (including a START button, a REPEAT button and a STOP button). The Control Panel 10 has various input and output connections (jacks) for receiving connection to motion and pressure sensors (e.g., 73R, 73L, 77R, 77L) and also includes an audio out connection (jack) 25 to allow a user to connect a headset. Naturally, wireless connections (such as Bluetooth) could be used in lieu of any of the hardwired connections to connect sensors, headphones or other components to the Control Panel 10. Wireless connectivity may be necessary when movement/ pressure sensors located on the user (such as in the user's shoes or on the user's clothing) are used instead of sensors attached to the exercise machine.

The Control Panel 10 also includes an audio player dock 27 to allow the user to connect an audio player (e.g. MP3 player, smartphone, tablet etc.) to the control panel. The Control Panel 10 also includes a memory card reader slot 23 to allow a user in insert a memory card containing data such as audio data (music) and/or biographically/user data. Naturally, user devices with wireless communication capability could communicate with the Control Panel 10 wirelessly, if desired.

The pause cue display 30 is preferably a simple easily visible and understood indication of the time remaining until the next interval begins. As shown in FIG. 1, the pause cue display may be a series of lights that sequentially change appearance (color or on/off) from top to bottom to depict the time remaining.

The laser light beam projector 37 may be a simple laser beam flash of a visual cue (described below) or it may be used a projector of the type used to project ("paint") an image onto a surface of the exercise equipment. This is especially useful in the context of a treadmill where the foot platform surface is moving under the user's feet or while seated on an exercise bike where the context relates to how the user is bending the arms and positioning the hands. Laser light beam projector 37 could project visual cues ranging from simple light flashes to lines of demarcation indicative of time intervals associated with beat sequences or GDM sequences.

The laser light beam projector comprises a laser projector or scanner 37 controlled by a laser light beam control engine 770. Sophisticated laser projectors now available modulate a laser beam to project a raster-based image. The systems work either by scanning the entire picture a dot at a time and modulating the laser directly at high frequency, much like the electron beams in a cathode ray tube, or by optically spreading and then modulating the laser and scanning a line at a time, the line itself being modulated in much the same way as with Digital Light Processing (DLP). This technology produces the broadest color gamut available in practical display equipment today, because lasers produce truly monochromatic primaries. The laser signal is modulated by introducing the video signal to the laser beam by an acousto-optic modulator (AOM) that uses a photorefractive crystal to separate the beam at distinct diffraction angles. The beam must enter the crystal at the specific Bragg angle of that AOM crystal. A piezoelectric element transforms the video signal into vibrations in the crystal to create an image. Horizontal and vertical refresh is achieved by a rapidly rotating polygonal mirror to give the laser beam the horizontal refresh modulation. The beam reflects off of a curved mirror onto a galvanometer-mounted mirror that provides the vertical refresh. Another way is to optically spread the beam and modulate each entire line at once, much like in a DLP, reducing the peak power needed in the laser and keeping power consumption constant. While this structure produces high quality projected images, other technologies may be more appropriate when cost is taken into account. As a less costly alternative, a laser scanner may be used. Laser scanners consist of small mirrors that are mounted on galvanometers to which a control voltage is applied. The beam is deflected a certain amount, which correlates to the amount of voltage applied to the galvanometer scanner. Two galvanometer scanners can enable X-Y control voltages to aim the beam to any point on a square or rectangular raster. This enables the laser lighting designer to create patterns.

Other methods of creating images through the use of galvanometer scanners and X-Y control voltages can generate letters, shapes, and even complicated and intricate images.

A sensor system is provided to detect user movement. The sensor system preferably is able to distinguish between movement of the user's right and left limbs (usually legs and feet) and may also be able to distinguish arm and hand movement and the pressure applied to the foot platform and other parts of the cardio fitness machine. The sensor system may include a time-of-flight camera system and/or an array of motion sensors that detect motion is specific zones of movement. The sensor system my further include pressure sensors for sensing pressure applied to the foot platform of the cardio fitness machine. The presume sensors may be applied on the foot platform, under a treadmill belt or in a user's show. Sensors may also be worn by the user when attached to/embedded in user's apparel, arm bands or shoes.

As shown in FIG. 1, the Control Panel 10 may include a time-of-flight camera system 39 to track user movements. Any known time-of-flight camera system may be used. An embodiment of the time-of-flight camera system may include the following components: Illumination unit (preferable infrared); Optics (a lens arrangement that gathers the reflected light and images the environment onto the image sensor, optical band pass filter only passes the light with the same wavelength as the illumination unit); Image Sensor (each pixel measures the time the light has taken to travel from the illumination unit to the object and back); Driver Electronics to control the illumination unit and the image sensor have to be controlled by high speed signals; and a Computation/Interface to calculate distance.

Various sensors may be wired to or otherwise in communication with the Control Panel 10. In the embodiment shown in FIG. 1, left 73L and right 73R motion sensors and left 77L and right 77R foot pressure sensors are connected to the Control Panel 10. The motion sensor heads preferable include both movement sensors and LED lights that can provide a visual cue (as described below).

The Control Panel 10 and sensors 73, 77 are designed to be mounted to a base and placed in proximity to a cardio-fitness machine so that the left and right pliable arms upon which the sensor heads are mounted can be arranged to a suitable position to detect motion in a defined zone of exercise space, for example, near the foot platform of the cardio-fitness machine and toward the constrained path of motion unique to the mechanics of the machine to detect foot motion or near the handles to detect arm motion. The motion sensors 73L, 73R are preferably located at the end point of adjustable gooseneck supports attached to the cardio-fitness machine or Control Panel 10 on an exercise bike with additional motion sensors located beneath the bicycle seat and on the handle bar as appropriate. The inner spaces of the tubes of gooseneck are used as cable laying paths for the power cables and signal cables for the motion sensors 73. The number of sensors is not limited to that of this embodiment and may include several provided it can operate in a manner similar in support of the method. The motion sensor 73R has a detection range of the exercise space constrained rightward by the path of motion of the fitness machine's foot platform. The motion sensor 73L has a detection range nearest the left foot platform and the exercise space constrained leftward by the path of motion of the fitness machine's foot platform. Each sensor is integrally provided with a light emitting element (LED) 73Q and a motion sensing (e.g., light detecting) element 73*s*. When a part of the user's body enters the detection range within the exercise space, light from the light emitting element is blocked and cannot be received by the corresponding light detecting element. Motion detection is realized by detecting such a state. In a mode whereby the lack of detection is made upon the cessation of movement e.g. the lack of the lower extremity entering the range of detection within the exercise space, the unblocked sensor emits a visible signal simultaneously with the upper extremity entering the range of detection within its exercise space. The visible signal making realized a light cue for a goal directed movement to be performed.

The foot pressure sensors 77L, 77R may be any known pressure sensor/transducer technology with associated power supply, transmitters and microcontroller. An exemplary embodiment uses a piezoelectric sensor that uses the piezoelectric effect to measure pressure, acceleration, strain or force by converting them to an electrical charge. Piezoelectric sensors may be located on the foot platforms of elliptical or AMT machines and under the moving belt of a treadmill. Sensors may also (or alternatively) be located in the user's footwear using, for example, the Nordic Semiconductor SoC (System-on-chip) design Microchip Technology PIC16F688 microcontroller; 3V Lithium 2032 battery and a 30 mm-diameter piezoelectric sensor.

The Control Panel 10 may include various wireless communication technologies. As described, above Bluetooth may be used for exchanging data over short distances. Wi-Fi or a similar protocol may be used to exchange data over a local or Global Information Network (GIN). In this way, the Control Panel 50 may access data stored in "cloud storage" data bases 55 or over the Internet, which may be beneficial as described below.

Figure 2:
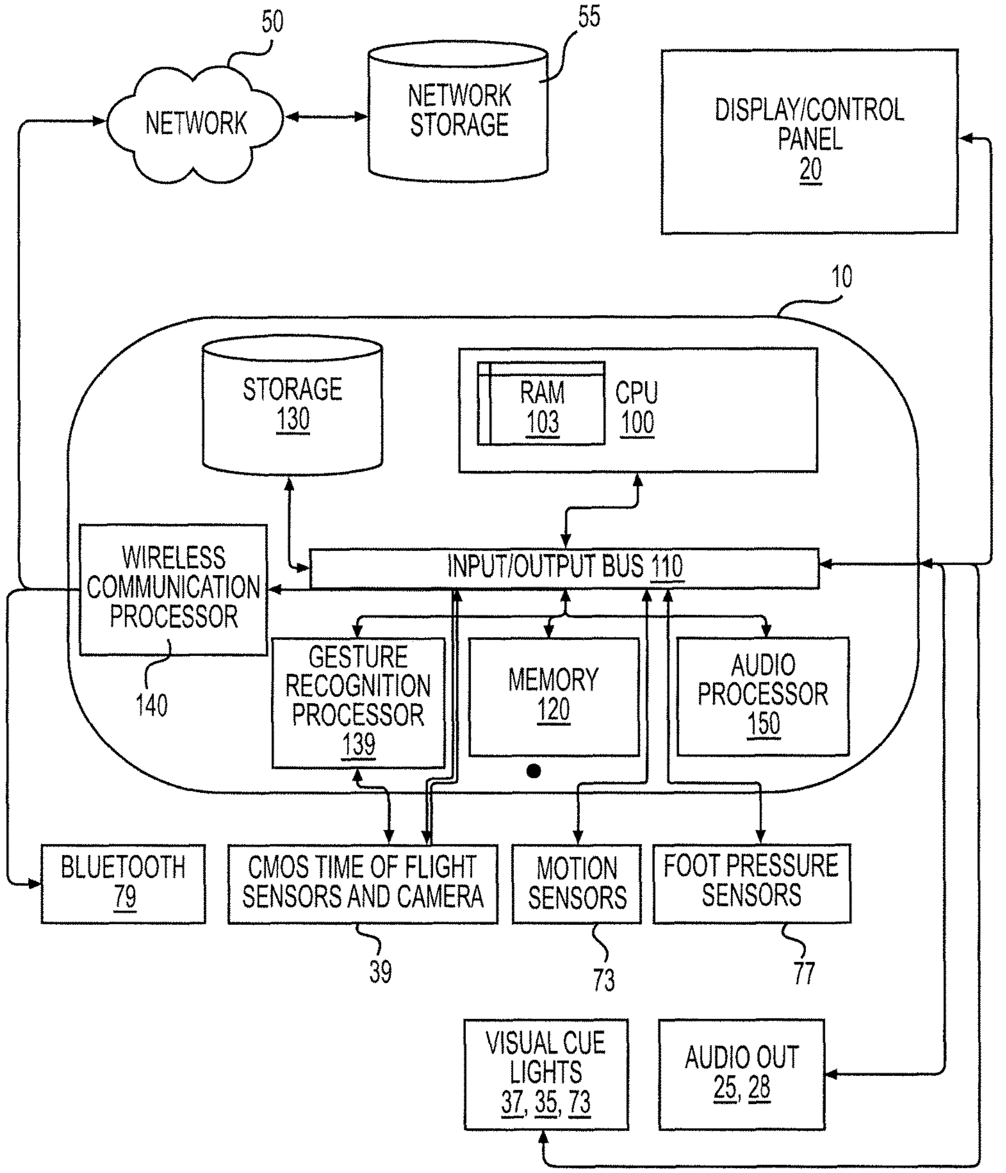
FIG. 2 depicts the System Architecture of an embodiment of the invention.

FIG. 2 depicts the System Architecture of an embodiment of the invention. As depicted much of the hardware is contained within the housing of the Control Panel 10. The hardware includes a CPU 100 with on board RAM 103; an input/output system bus 110 (including control bus, address bus and data bus functionality); system memory 120; system storage 130 (flash or hard drive); a gesture recognition processor 139 (if the system includes time-of-flight sensing capability); and a wireless communication processor for enabling Wi-Fi, Bluetooth and/or other wireless data exchange over a local or global information network 50.

The system also includes an Audio Processor 150 for providing digital audio and beat information to the system. The Audio Processor 150 may include a beat data extraction engine 730 for extraction of beat information from a music sample. The Audio Processor 150 also includes digital audio encoders and decoders as necessary to process music files. Pulse-code modulation (PCM) may be used to encode music as a digital signal. A digital-to-analog converter performs the reverse process, and converts the digital signal back into an audible sound.

Improvements in beat detection will offer more options for a listener to base his impressions on including note onsets, drumbeats and patterns, and harmonic changes. As such, it is possible to expand the concept of what is a beat by including what is not exactly a beat per se, but what humans may perceive a beat to be. Experienced users may do this when extracting beats to match a GDM to. In the digital format, music from a digital (MP3 for example) file can be converted and subdivided into another form of representation. For instance algorithms may achieve such a conversion by locating the number of highest amplitudes corresponding to number of beats in a song and store those instances as values for some sort of future processing. Once retrieved, these values offer location details to formulate a multi-faceted rhythm map. In this format, such a map can be used for several purposes within a system that integrates musical phrases. For instance, a comparison between this map and newly obtained digital information may be understood to have different meaning in a new context. That features of the musical information offer new variables from such data sets is relevant to the present system and method for rhythmic cuing. The present inventor recognizes that as methods become more sophisticated they will match the capabilities of the auditory pathways in retrieving information about sounds in music.

Whereas algorithms look for periodic peaks of a particular feature to represent the beat events in a musical phrase, others will be devised and improve upon current methods of beat detection. A reason for the improvement stems from the amount of variability within the human auditory system and that when listening to music humans form impressions of what a beat is from the multi-faceted representations of information within of a song. Improvements in beat detection will offer more options for a listener to base his impressions on including note onsets, drumbeats and patterns, and harmonic changes. Obtaining sound information at this level will require more than one type of detection to be made at a time. The inevitability of more than a single beat detector launched simultaneously will improve the overall accuracy and experience of a system and method of the present invention. Several monitors aggregating information from multiple detectors would generate a more advanced beat tracking response over an individual detector operating independently. This improvement in digitizing music will benefit usage of the present invention and the ability to achieve the objective of performing goal directed movements in response rhythmic cuing.

As shown in FIG. 2, the Control Panel 10 receives input from Bluetooth 79 and other wireless sources 50; the time-of-flight sensors and camera 39; the motion sensors 73; and the foot pressure sensors 77. The Control Panel may output signals to each of these components and also outputs control signals and engages in data exchange with the visual cue lights 35, 37, 73; the touch screen panel 20 and the audio out sources 25, 28.

Figure 3:
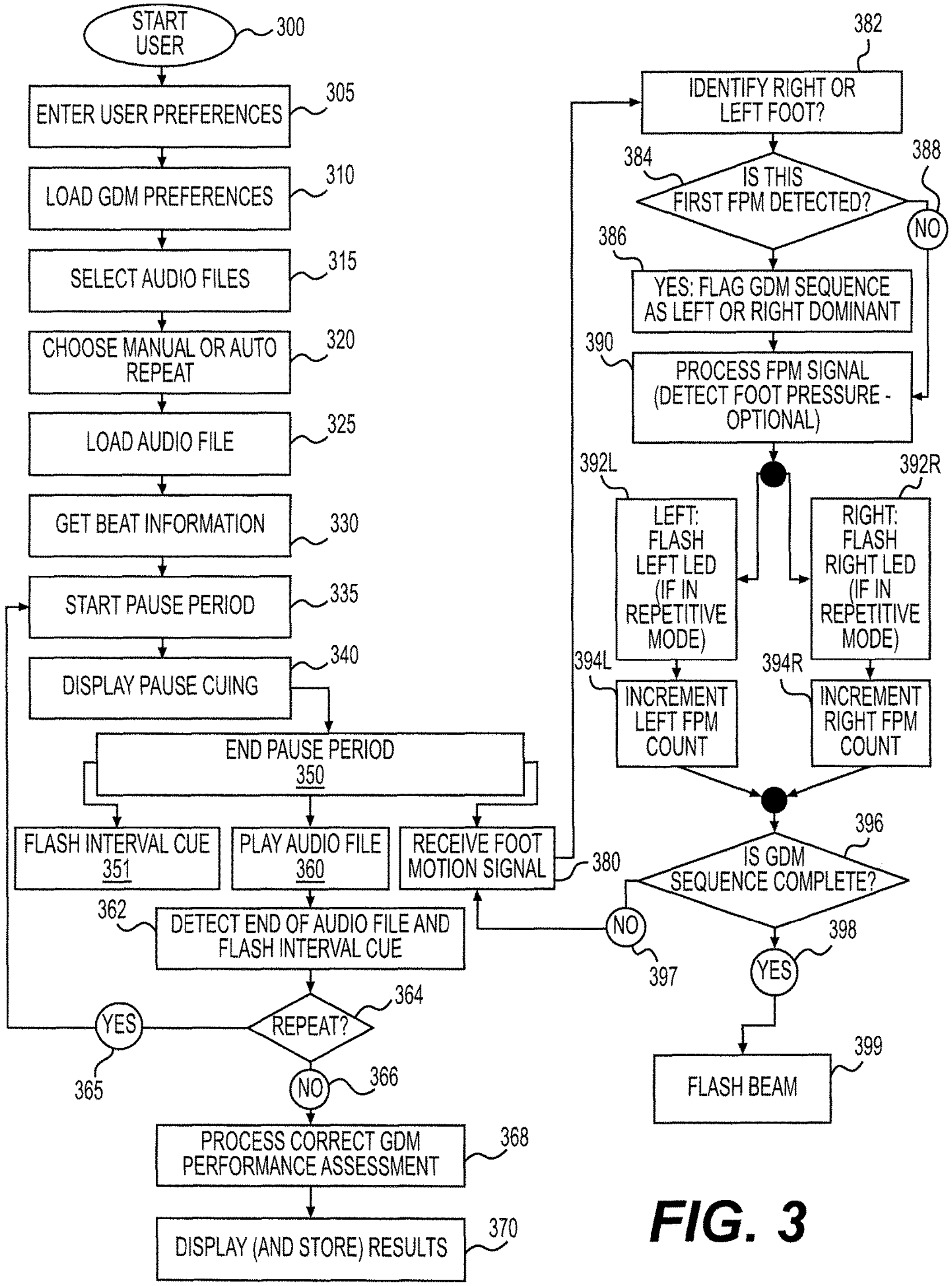
FIG. 3 is a flowchart showing operation of an embodiment of the invention.

FIG. 3 is a flowchart showing operation of an embodiment of the invention. As shown, the process begins with the user initiating the process at step 300 (such as by pressing the start button 40). At step 305, the user enters preferences and other user specific information including for example a USER ID that allows the system to retrieve records from local storage 130 or cloud storage 55. At step 310, the system loads data related to the preferred Goal Directed Movement (GDM) sequence including, for example, the number of GDM in the sequence, the left-right sequence of GDM and, if desired, the spatial orientation of each GDM, i.e. in the upper limbs, in the lower limbs, or simultaneously in both.

GDM sequences are a set number of GDM's performed in series according to a method suitable to the particular cardio-fitness machine. A pattern of GDM's is comprised of alternating foot movements on and with Foot platform or pedals on a stationary exercise bicycle and its constrained path of motion. For instance, a foot platform on a treadmill belt is the rotating singular rubber belt; an elliptical trainer has pedals that function as a Foot platform that rotates in tandem; and the Foot platform of an AMT Adaptive Motion Trainer function in a dual plane of resistance, up and down and back and forth in each instance the system can monitor movement of the upper limbs simultaneously with the lower limbs. The number of movements on and with the Foot platform varies according to the GDM selected and the objectives and preferences unique to the user's performance whereby a same GDM sequence can be repeated and assessed; or the assessments made can be inclusive of various GDM sequences performed according to the entry preferences of the user including those preferences available for the upper limbs.

GDM preferences will be reflective of the particular audio file(s) selected and most importantly, the number of beat events in the musical phrase comprising the audio file selection as the objective of achieving the pattern in the GDM sequences is to match GDMs to a beat in the phrase.

At step 315, an audio file is selected. The selected audio file functions as sound content representing the beat events in a musical phrase. The sound information is processed into a set number of beat events, which during the performance of a GDM sequence, guide the user's movements to be coincident with light emissions. PCM information formatted into Mp3 files supplies the content of sound information. The digital information is subsequently reformatted to meet the present invention's requirement for processing i.e., extracting beat information. User preferences for selected audio files will correspond to the user preferences for GDM sequences. Audio files may be obtained in the form of an entire song or as a component of a song i.e. a musical phrase. Audio files can be categorized according to beat event information for the purposes of matching GDM sequences to them and selected on the basis of their compatibility.

At step 320 a selection is made (either manually or from user preferences) as to whether the audio file (musical phrase) will be automatically repeated one or more time or repeated only in response to user input (such as the REPEAT button 40) At step 325, the audio file—preferably representative of a musical phrase—is loaded into the system. At step 330, the system gets beat information with respect to the selected audio file. The beat information may be extracted by the audio processor 150 or obtained from local storage 130 or network storage 55. The beat information includes information as to the number and timing of the beats in the audio file. As noted above in connection with the discussion of the beat extraction engine 730, more sophisticated beat detection/extraction (such as the creation of a multi-faceted rhythm map from the digital audio file) may be used as the technology becomes more readily available.

At step 335 a pause period begins. The duration of the pause period—which is the time between successive playing of the audio file—may be determined based on user preferences, user input or user performance as determined by the system. At step 340, pause cuing is displayed on the pause cue display 30. In the embodiment shown in FIG. 1, a series of eight blocks of light are illuminated and then turned off one by one from top to bottom to cue the user as to the end of the pause period.

At the end of the pause period 350 three things happen substantially simultaneously. At step 351, a flash interval cue is provided to the user. In the embodiment shown in FIG. 1, the flash interval cue is provided by an interval lamp 35 on the Control Panel 10. At step 360, the audio file begins to play and audio output is provided through the audio out jack 25 or through the speaker 28. At the same time, as shown at step 380, the system begins to look for signals from the sensors, e.g., the sensors that monitor the user's foot motion [motion and/or pressure] or hand or arm movement. An exemplary process of monitoring the user's upper and lower limb GDM movement is depicted at steps 380-399 described in detail below.

Briefly, as noted, pause cuing is displayed prior to the onset of audible musical phrase. At end the pause period a first beat in the phrase becomes audible, and is synchronous with a visible signal emitted from the control panel. The signal flashes as an interval cue. The audio file begins to play. The GDM sequence begins. At the end of the audio file, a signal flashes an interval cue lamp 35. If the user preference has instructed the audio file to repeat the audio file, a new pause period starts and the user resumes the performance of a GDM sequence with the foot laterally opposite the one that commenced the previous GDM. A correct GDM sequence performance assessment will be judged according to the user preferences for the number of GDM's in the sequence selected.

The end of the audio file playback is detected at step 362 and a flash interval cue is made using the interval lamp 35. The system then determines if audio file playback is to be repeated (at step 364). If YES (step 365), the process returns to step 335 and the pause period begins. If the desired number of playbacks has been reached or if manual repeat was selected at step 320, the playback ends (step 366) and the system processes a correct GDM assessment at step 368 and proceeds to display and store results at step 370. The results may be stored in local data storage 130, on a memory card reader 23 or in network storage 55.

Steps 380-399 depict one exemplary process of monitoring the user's GDM movement. It should be understood that with the use of enhanced sensing such as the CMOS time of flight sensors and camera 39 and gesture recognition processor 139, it is possible to monitor and assess user performance of GDM with great precision. It is also possible to monitor users GDM performance by applying Bluetooth 79 or other wireless sensors to extremities (in user's apparel or bands worn by users). However, many benefits of the invention are achievable by monitoring a user's foot motion and perhaps foot pressure, in addition to monitoring the user's arm and hand movements applied to equipment as described hereinafter.

At step 380, the system receives a signal indicative of motion detection (a foot motion signal in the illustrated example). At step 382, the system determines whether the motion is associated with a right limb or a left limb. In the illustrated example, the system determines if the foot motion signal came from a right sensor 73R or a left sensor 73L. At step 384, the system determines whether that limb motion (e.g., foot motion) signal received is the first limb (e.g., foot) motion signal of this GDM sequence. In general it is desirable to begin and end each of the GDM sequences according to the present invention with motion of the same foot or arm. Thus, if a GDM sequence begins with left foot (or arm) movement, it should end with left foot (or arm) movement. The next iteration of the GDM sequence (after the pause) will then begin with right foot (or arm) movement and end with right foot (or arm) movement. Thus, if (at step 384) it is determined that the foot motion signal is the first foot motion signal of the GDM sequence, then the GDM sequences is flagged according to whether the movement was a left foot movement (sensor 73L) or a right foot movement (sensor 73R). If the foot motion signal is NOT the first foot motion signal of the GDM sequence, then step 386 is skipped at step 388.

At step 390, the limb (foot or arm) motion signal is processed by, for example, recording its timing, left or right and, optionally, other characteristics such as pressure, velocity, direction, acceleration etc. In the illustrated example reference is made to foot motion, but the sequence could also be used with regard to signals indicative of arm movement (detected by a time of flight sensor, for example). The foot pressure sensors 77L, 77R or wireless sensors 79 are used for detecting foot pressure while the sensors and camera 39 and gesture recognition processor 139 may be used for detecting other motion characteristics. When a left foot motion signal is detected, the system may flash the Left LED (preferably located on the left sensor head 73L) at step 392L. The system then increments the Left FPM (foot platform motion or foot motion signal) count by one at step 394L. Likewise, when a right foot motion signal is detected, the system may flash the Right LED (preferably located on the right sensor head 73R) at step 392R. The system then increments the Right FPM count by one at step 394R.

At step 396, the system then determines whether the GDM sequence is complete by, for example comparing the number (and possibly sequence) of foot motion signals received to the number of FPM corresponding to the GDM sequence loaded at step 310. Regardless of the precision used to monitor GDM performance, the determination that the sequence is complete is made by comparing specified number of GDM to detected GDM.

Information obtained from the user preferences (at step 305) is used to determine if the GDM Sequence is complete. In correct sequencing, the first and last GDM is detected by a same sensor so that the next performance can begin on the laterally opposite side. However a smooth transition is not always a given. An uneven number of GDMs in a pattern work best for an initial and final detection to be made. In the event there is an even number of GDMs in a pattern, the pause period aids in a smooth transition so that the side laterally opposite can initiate the next GDM.

Interval only GDM sequences are detected by the same sensor twice i.e., one detection for the first beat and one detection for the last beat, at the beginning and end of the musical phrase, initiated by a right or left dominant performance. In the event the music ends, the GDM is complete. If the musical phrase is audible and the GDM sequence resumes after left or right foot motion detection, the number of GDM in the users preferred GDM sequence is not yet achieved and the performance continues according to the method until the music ends.

In repetitive mode, the number of detections is more than two. The number of detections in repetitive mode is always upwards of three i.e., at least one more detection must be made in the pattern of detections other the initial detection and the final detection. According to the method said detections are made by the same sensor. In other words, for every complete left or right initiated GDM sequence performance, the pattern of detection to be made next has the sensor laterally opposite entering a detective state.

At step 397, if the GDM sequence is not yet complete, the system returns to step 380 and receives the next foot motion signal or arm motion signal. If the GDM sequence is complete, at step 398, the system proceeds to step 399 and a visual cue indicating the completion of the GDM sequence has been detected is displayed. The embodiment shown, the visual cue is made by flashing a laser beam at step 399 using, for example, the laser light beam projector 37.

By receiving Interval cues only, and if the user preferences specifies manual input of the audio file, a beam will flash to signal that the GDM sequence is completed. Audio files that play repeatedly according to user preferences based on their compatibility with a GDM sequence in use will receive a flash beam after the repetition of the pattern within the selected GDM sequence is complete. If more repetitions of GDM are required by the system to meet the specified user preference the flash beam will not appear until the end of the musical phrase.

It should be recognized that the timing of the flash interval cue of step 362 (signifying the end of audio playback) and the laser beam flash of step 399 (signifying the completion of the GDM sequence) are independent of one another. However, performing the GDM sequence so that these two signals are in (or near) synch is an important user objective of the invention. Moreover, synching the flashing of sensor LED'S 73L and 73R (at steps 392L and 392R) with the beats of the audio signal is indicative of highly desirable rhythmic entrainment. Thus, the system and process described above provide a tool to allow users to exercise rhythmically.

Before describing use of the invention further, embodiments of the invention in the context of several types of cardio-fitness machines will described with reference to FIG. 4 (an adaptive motion trainer); FIG. 5 (an elliptical machine) and FIG. 6 (a treadmill). By virtue of these examples, those skilled in the art will understand that the invention may be adapted for use in other cardio-fitness machines.

Figure 4A:
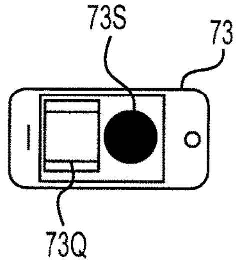
FIG. 4A is a schematic view of one form of sensor head according of to an embodiment of the invention.
Figure 4:
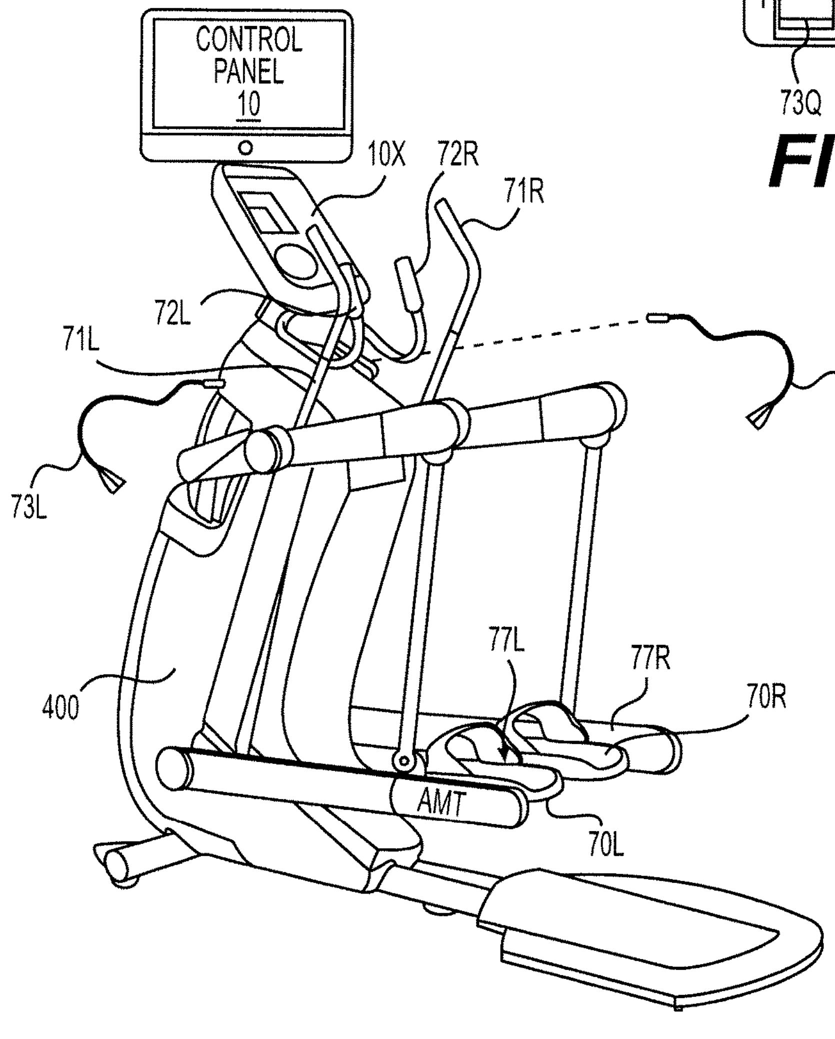
FIG. 4 is a partially schematic perspective view of an adaptive motion trainer [AMT] exercise machine according of to an embodiment of the invention.
Figures 5, 5A:
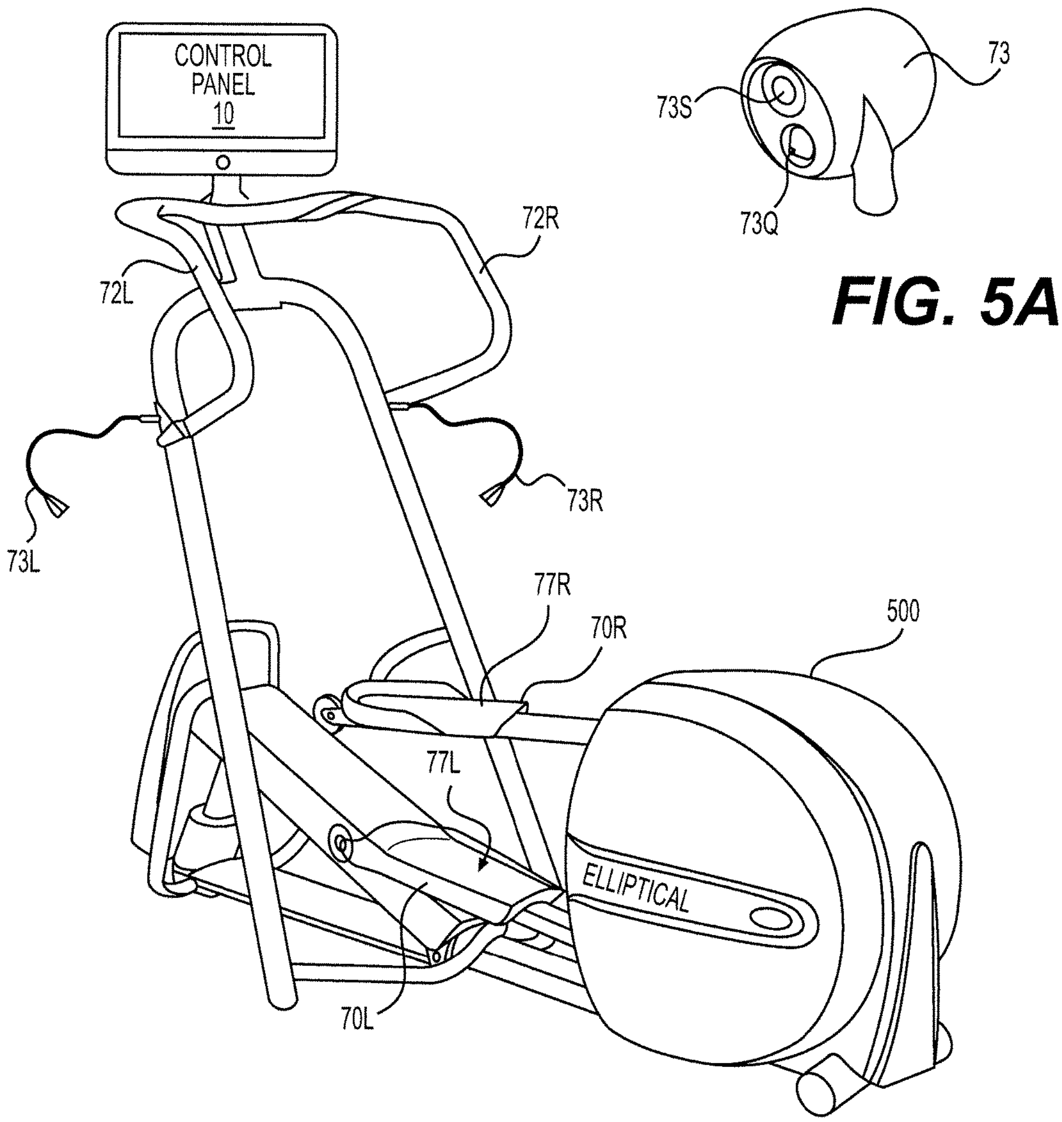
FIG. 5 is a partially schematic perspective view of an elliptical exercise machine according of to an embodiment of the invention.
FIG. 5A is a perspective view of another form of sensor head according of to an embodiment of the invention.

FIG. 4 is a partially schematic perspective view of an adaptive motion trainer [AMT] 400 exercise machine according to an embodiment of the invention. As is known it the art, the AMT body 400 includes mechanical linkages and controls to guide user motion. The AMT further includes a left foot platform 70L and a right foot platform 70R; a left movable arm 71L and a right movable arm 71R; left and right fixed arms 72L, 72R; a left foot movement sensor 73L that includes a head mounted on an adjustable gooseneck support and a right foot movement sensor 73R that includes a head mounted on an adjustable gooseneck support. Foot pressure sensors 77L, 77R are located on the respective foot platforms. Pressure sensors 77L, 77R may also be provided on the movable arms 71L, 71R at locations that the user is likely to grasp or on sleeves that are slidable along the arms and lockable at positions along the arms. A Control Panel 10 of the type described above is provided at a convenient location and the AMT may include additional controls 10*x*.

FIG. 4A is a schematic view of one form of sensor head according of to an embodiment of the invention. The sensor head includes a motion sensor portion 73*s* and a LED light 73Q that can be used to provide the left and right flashed of steps 392L and 392R described above.

FIG. 5 is a partially schematic perspective view of a simple elliptical exercise machine 500 according to an embodiment of the invention. The machine body includes known mechanical linkages and controls to guide user motion. The elliptical further includes a left foot platform 70L and a right foot platform 70R; left and right fixed arm portions 72L, 72R; a left foot movement sensor 73L that includes a head mounted on an adjustable gooseneck support and a right foot movement sensor 73R that includes a head mounted on an adjustable gooseneck support. Foot pressure sensors 77L, 77R are located on the respective foot platforms. As is known, the elliptical machine may also include a left movable arm and a right movable arm. Pressure sensors 77L, 77R may also be provided on the movable arms at locations that the user is likely to grasp or on sleeves that are slidable along the arms and lockable at positions along the arms. A Control Panel 10 of the type described above is provided at a convenient location.

FIG. 5A is a perspective view of another form of sensor head according of to an embodiment of the invention. The sensor head includes a motion sensor portion 73*s* and a LED light 73Q that can be used to provide the left and right flashes of steps 392L and 392R described above.

Figure 6:
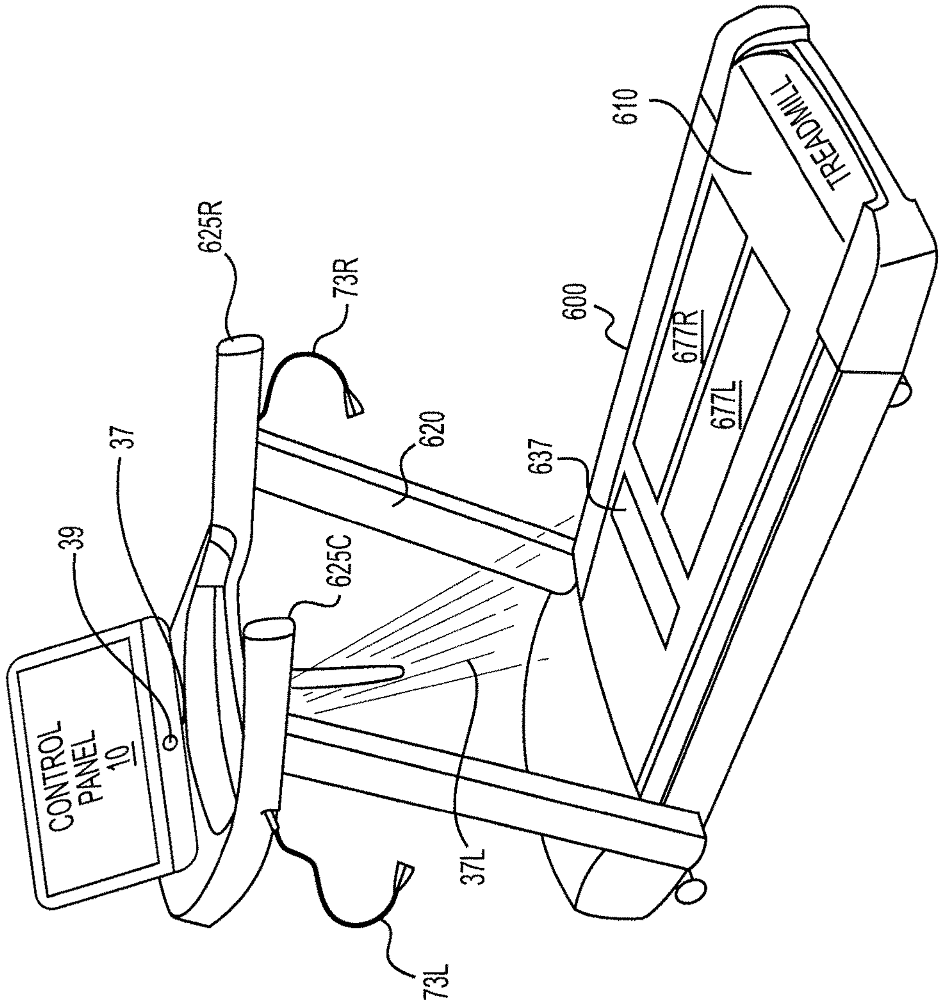
FIG. 6 is a partially schematic perspective view of a treadmill exercise machine according of to an embodiment of the invention.

FIG. 6 is a partially schematic perspective view of a treadmill exercise machine 600 according to an embodiment of the invention. As is known, the treadmill includes a body 600 that includes a base that houses a motor for driving a belt 610 that serves as a movable foot platform for exercise. An upwardly extending support 620 provides left and right arm portions 625L, 625R and a support for a Control Panel 10 of the type described above. The treadmill further includes a left foot movement sensor 73L that includes a head mounted on an adjustable gooseneck support and a right foot movement sensor 73R that includes a head mounted on an adjustable gooseneck support. Because the belt 610 moves and wears over time, it is not practical to provide pressure sensors on the belt. Instead, a left pressure sensitive region 677L and a right pressure sensitive region 677R are provided under the belt 610 to allow detection of foot pressure on the belt corresponding to left and right foot pressure. Characteristics of foot and arm limb movement may also be detected by the time-of-flight sensors and camera 39 of the Control Panel 10.

When using a treadmill, it may be advantageous to provide lines of demarcation visible on the moving belt to guide user movement. With the computer controlled laser light bean projector 37 of the invention, it is possible to project images of lines of different colors onto the belt 610. The image of the lines of demarcation may be stationary or moving at a desired pace. Projecting images onto the equipment is a simple form of augmented reality. A headset may be connected to the control panel 10 and worn by the user to provide an enhanced virtual or augmented reality experience. As shown in FIG. 6, the laser light beam projector 37 projects a beam 37L that creates the image of a line of demarcation 637 on the belt 610.

Figure 9:
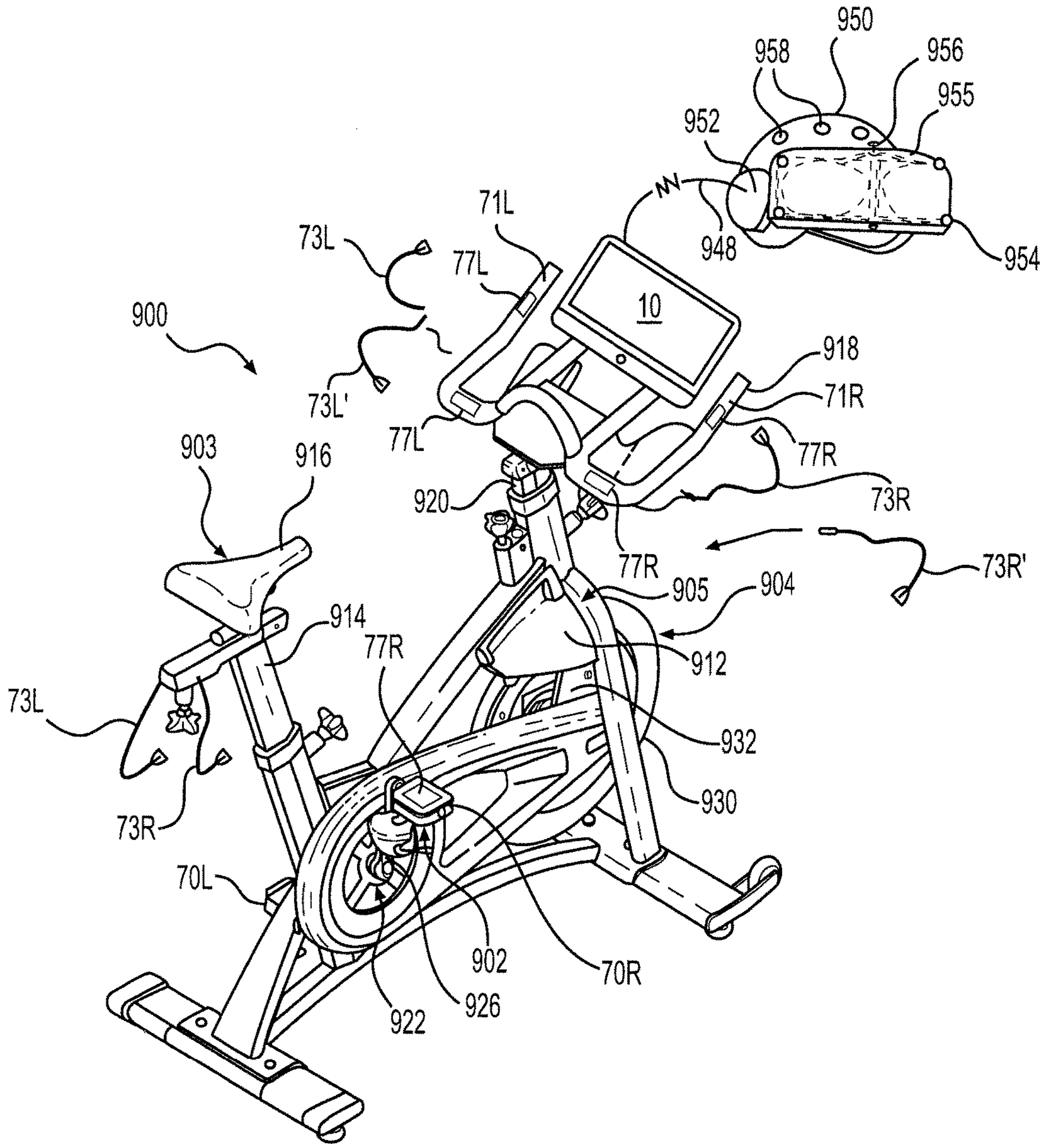
FIG. 9 is a partially schematic perspective view of a stationary exercise cycle machine according to an embodiment of the invention.

FIG. 9 is a partially schematic perspective view of a stationary exercise or indoor cycling bike. Exercise bikes typically include a flywheel rotated by a user via a drive train system. Resistance to rotation of the flywheel may be provided by an eddy current brake positioned proximate the flywheel or by a roller manually tightened to provide resistance.

FIG. 9 shows a perspective view of an exercise or indoor cycling bike 900, which may be referred to herein as either of the above. FIG. 2 shows a perspective view of a portion the exercise bike 900 with the shrouds removed to show portions of the drive train assembly 902 and the resistance assembly 904. The exercise bike may include a frame 905, a seat assembly 903, a handlebar assembly 918, the drive train assembly 902 and a resistance assembly 904.

As shown, the stationary exercise bike (cycle) 900 further includes a left foot platform 70L and a right foot platform 70R; a left arm 71L and a movable arm 71R. The arms 71L, 71 (may be fixed or movable. A plurality of left movement sensors 73L that include a head mounted on an adjustable gooseneck support and a plurality of right movement sensors 73R that include a head mounted on an adjustable gooseneck support. Possible positions of the gooseneck supports are illustrated in FIG. 9. Sensors 73L, 73R are shown mounted on a seat post 914 under a seat 916, to handle bars 918 and to a frame 905. By altering the position of the support, the sensors can be aligned to detect motion in specific zones of movement and thus distinguish between movement of the user's right and left limbs (legs and feet and/or arms and hands). The sensor system also detects the pressure applied to the foot platform and other parts of the cardio fitness machine. The sensor system may include a time-of-flight camera system and/or an array of motion sensors (provided in the control panel or separate therefrom) that detect motion is specific zones of movement. Foot pressure sensors 77L, 77R are located on the respective foot platforms 70L, 70R. One or more pressure sensors 77L, 77R provided on each of the bars (left and right) in the handle bar assembly 918. A Control Panel 10 of the type described herein is provided at a convenient location and the cycle may include additional controls. The exercise bike 900 may further include one or more shrouds or covers 912 joined to the frame 905 to limit access by a user or others to moving portions of the drive train assembly 902 and resistance assembly 904.

With reference to FIG. 9, the seat assembly 903 may include a seat post 914 adjustably connected to the frame 905 to allow the user to adjust the vertical position of a seat 916 for supporting the user in a seated position. The seat 916 may also be adjustably supported by the seat post 914 to allow the user to adjust the horizontal position of the seat 916. The handlebar assembly 918 may include one or more handles 918 for a user to grasp. The handles 918 may take the form of bull horns, aero bars or any other handle used on exercise bikes. A plurality of pressure sensors 77L, 77R are provided at locations where the user may grasp the handle bars to detect upper limb movement and force. The location of the pressure sensors may be adjustable to user preference by, for example, mounting the pressure sensors on a sleeve that slides along the handle bars and can be selectively locked into place. The handlebar assembly 918 may further include a handlebar post 920 connected to the frame 905 to allow the user to adjust the vertical and/or horizontal position of the handles 918.

The drive train assembly 902 may include a crank assembly 922 rotatably supported by the frame 905 and a drive train connection member 124 for operatively joining the crank assembly 922 to the resistance assembly 904. The crank assembly 922 may include a crank or drive ring rotatably mounted on the frame 905 at a bottom bracket, crank arms 926 extending from the drive ring, and a right foot platform 70R and Left foot platform (pedal) 70L joined to respective crank arms 926 for supporting the user's feet for movement along a constrained path and allowing the user to engage the crank assembly 922. Pressure sensors such as that shown at 77R may be provided on the pedal surface. The drive train connection member may be a chain, a linkage, a belt or any other suitable member for transferring rotation of the drive ring to a flywheel 930 of the resistance assembly 904. The resistance assembly 904 may include the flywheel 930 and a brake assembly 932. The flywheel 930 may be rotatably mounted to the frame 905. The flywheel 930 may be further joined to the drive ring by the drive train connection member (chain, linkage or belt) such that rotation of the drive ring causes rotation of the flywheel 930. The flywheel 930 may be directly joined to the drive ring via the drive train connection member (chain, linkage or belt) or may be joined via a clutch, as is known. The brake assembly 932 may be operatively associated with the flywheel 930 to resist or otherwise oppose rotation of the flywheel 930 using an eddy current braking system.

The system and process described above facilitate sensory rhythmic time cuing in exercise with the use of foot platform(s) of cardio-fitness machines. Concepts of rhythm are interpreted to be understood as time organization whereas rhythm can be a symmetric, even pulse, as found in a metronome beat; also found in metered rhythm in which even pulses are grouped by accent into repeated groups of 2, 3, 4 and so on; and in rhythmic patterns consisting of a repeated musical phrase wherein the pulses or beats have different numerical ratio e.g., a long beat followed by a short beat half as long as the previous one, followed by two even shorter beats twice as short as the previous one etc. Audible pulse patterns are recurring rhythmic motifs found in musical phrases. Sensorimotor assimilation of regularly occurring beat events is learnable. An ability to time movement is conventional in human movements of clapping, finger tapping and head nodding. Rhythms therefore can fixate a response interval for the execution of movement. Rhythmic cues aid in regulating the brain and body ever more smoothly across durations of movement. And smoothing of acceleration and velocity enables an optimization of movement paths and trajectories in more advanced, goal directed, movement tasks.

The present invention provides a novel way of utilizing rhythms to trigger human beat perception and musical period matching during exercise. Because the elements of a song are a series of musical phrases and because at least a musical phrase is integral to the present invention, rhythmic stimuli, along with the inventive method, has the effect not of a randomized response, but of a precise kinematic rhythmic interval. Each successful sensorimotor synchronization performance has the potential to improve the motor system's capacity for rhythmic entrainment.

Sensor detected movement on and with the foot platform(s) are exemplary of GDM objectives where audible pulse stimuli at the beat events in the musical phrase cue performance methods to synchronize with them. Beat events guide movement patterns to be performed with a left or right extremity in the upper or lower body or simultaneously with both where the numerical ratio of rhythmic stimuli encourages performances of response intervals with different tasks, i.e. while pedaling on a stationary exercise bike the user may twist the upper body so that the left extremity enters the exercise space associated with 71R and 73R where the next sequence of GDMs would begin with the right extremity entering the exercise space associated with 71L and 73L and where an excess of pressure may be applied to the pedal so that 77R detects that the user has intended to do so in anticipation of 77L entering its detection state simultaneous with either 71R and 73R or 71L and 73L according to the method when a musical phrase begins, and to complete with the same side of the body when the music phrase ends.

Visible pause displayed in between the musical phrases (the pause display cue 30 at step 340) orients the user to begin a next performance of the GDM with the opposite extremity. A visual fade on the display screen precedes the user hearing an audible pulse. According to the user's preference, a touch controlled screen may alter the speed of the visual fade on the display screen and thus the timing of the audio out to the speaker or headphones. The visible pause may be reduced or optionally omitted as the user becomes proficient at performing GDM sequences more rapidly to several musical phrases playing in a row and in the event of GDM sequences being performed during the course of an entire song.

When the pause period ends (at step 350) the user is cued to reproduce the pattern again beginning on the opposite side. Performing patterns of left to right to left movement on and with the Foot platform, followed by right to left to right, (or vice versa) in time with a beat, evidences rhythmic sensorimotor synchronization whereby movement of the user's lower extremity on the Foot platform is detected by the sensors and correspondence (number of beats in a musical phrase and coincidence of detections within a pattern) is evaluated and additionally where the user's upper extremity enters the exercise space associated with a right side movement or left side movement and the pattern of movements is detected by the sensors and correspondence (number of beats in a musical phrase and coincidence of detections within a pattern) is evaluated.

Such detections are made according to the method wherein at least a pattern of detection has been made and the sensor 73R has detected, the sensor 73L has detected, and the sensor 73R has a detected and whereas the same series of movement beginning on the left side are cued for a next performance where upon sensors 73L, 73R, 73L outputting signals, a visible signal successfully cued said performance.

Consequent to the above pattern of movement detection, a light cue from an LED within the sensor (73) provide immediate feedback that a correspondence (coincidence of an audible pulse (beat event) and coincidence of a detection within the movement pattern) was made.

The above detections may also correspond to the movement pattern's cessation e.g. the lack of the lower extremity entering the detection range of the exercise space and the unblocked sensor emitting a light beam in addition to or possibly exclusively where the upper limb enters the detection range of the exercise space. The visible signal making realized an interval cue for a next performance.

Additionally, movement may be detected by the sensors 73R, 73L, coincident with the light cues synchronized to the beginning and end of all musical phrases emitted from the interval lamp 35.

Light cues provide the user with immediate feedback that a coincidence between a beat in the musical phrase and a GDM was made. Lights cue the user in different ways according to the pattern of detection made. If an LED flashes during a performance of a pattern, the GDM detection is coincident with a beat in the musical phrase. This mode of feedback is obtainable in a user preference of repetitive cuing. When a beam flashes at the end of a pattern performance, the GDM detection is coincident with the last beat in the musical phrase, which also coincides with the completion of the GDM selected. This user preference is obtained in a user preference of interval cuing. Both forms of cuing are available to the user during a performance in addition to the system's interval cue (lamp 35), which is instructed to be synchronous with the first and last beat in any musical phrase selected. In either mode, Interval Cuing or Repetitive cuing, light cues correspond to the pattern of GDMs and the detections made while performing the pattern and the beginning and end of the music.

The following descriptions are exemplary of goal directed movement (GDM) sequences performed on and with the foot platforms of the cardio-fitness machines described above, namely an Adaptive Motion Trainer (AMT) 400, an Elliptical trainer 500, and a treadmill 600 and a stationary exercise bike 900 whereby rhythmic sensorimotor synchronization is achievable according to the invention.

AMT

Following the pause period, at the start point in the first position GDM, a right foot platform 70R and left foot platform 70P of an AMT 500 are level with each other. In a second GDM a user engages the lower extremity to depress a Foot platform and third makes allowance for the Foot platform to return to the first position. The machine's mechanics force the Foot platform to rise. In this third GDM the user controls the level the Foot platform can rise to—e.g. the start point whereby the Flash beam cue appears and the beats in the rhythmic phrase selected end simultaneous with the positioning of the Foot platform. Motion then resumes from the start point in the first position on the first beat in a musical phrase using the opposite foot platform. The user presses down on the Foot platform in time with the beat and the Foot platform rises to the next beat. The final sound signal i.e., the last of the beats in a musical phrase having a grouping of beats, corresponds to the cessation of movement e.g. the lack of foot motion and as such no detection is made and the unblocked sensor emits a visible signal.

The sensors 73R, 73L, 73R successively having detected a pattern of movement in the Foot platform's being depressed in tandem may signal an LED whereby the flashing light feeds back visual information for the performance to continue as specified (referred to as Repetitive mode where the sensor LED 73Q flashes at each GDM).

Also sensor 73R having detected twice in the interval corresponding to the first and last beats in a musical phrase, is synchronous with a light cue emitted from an interval Lamp 35 at the musical phrase's beginning and end. Laser Light Beam Projector 37 emits a flash beam simultaneous with detecting sensor 73R upon the determination that the sequence is complete by comparing specified number of GDM to detected GDM.

The sensors 73L, 73R, 73L successively having detected a pattern of movement in the Foot platforms being depressed in tandem may signal an LED whereby a flashing light feeds back visual information for the performance to continue as specified (referred to as Repetitive mode where the sensor LED 73Q flashes at each GDM).

Also sensor 73L having detected twice in the interval corresponding to the first and last beats in a musical phrase, is synchronous with a light cue emitted from an interval Lamp 35 at the musical phrase's beginning and end. Laser Light Beam Projector 37 emits a flash beam simultaneous with detecting sensor 73L upon the determination that the sequence is complete by comparing specified number of GDM to detected GDM.

Elliptical Trainer

In the start position the user exerts an uneven pressure on each Foot platform. A light cue (LED) appears respective to the Foot platform receiving more force, the rotation of which matches the beats in the rhythmic phrase (audio signal) selected. A GDM using the Foot platforms of an Elliptical Trainer is movement whereby at the start point in the first position GDM one Foot platform is in a low position closest to the floor and the adjacent Foot platform is in a high position furthest from the floor. The user motions the low Foot platform more aggressively in a manner similar to operating a skate board or similar motion controlled device where accelerated movement is achieved more so with one foot than the other. In this instance, one of the Foot platform's movement along its constrained path of motion is applied more pressure to in order to achieve a desired speed corresponding to the beats in the musical phrase. The Foot platform laterally opposite, although traveling at the same speed (due to the machine's constraints on motion performance while on board), is used to keep the user's balance. As such the user's feet hold different positions during performance—the foot exerting the pressure is flush with the Foot platform the other is on tip toe.

The pressure sensors 77R and 77L detect rightward and leftward pressure on a foot platform respectively. For each rotation of a Right Foot platform, a pressure sensor 77R having detected, a comparator outputs successively the Foot platform's detection in comparison to the pressure sensor 77L and thus greater motion made with the right foot.

For each rotation of a Left Foot platform a pressure sensor 77L having detected, a comparator outputs successively the Foot platform's detection in comparison to the pressure sensor 77R and thus greater motion made with the right foot.

In addition the light emitting sensors 73R and 73L detect rightward movement of a foot platform and leftward movement of a foot platform coincident to a beat in the musical phrase.

For each rotation of the Right Foot platform a light emitting sensor 73R having detected in conjunction with a pressure sensor 77R, a flashing light feeds back visual information for the performance to continue as specified (referred to as Repetitive mode where the sensor LED 73Q flashes at each GDM).

For each rotation of the Left Foot platform a light emitting sensor 73L having detected in conjunction with a pressure sensor 77L, a flashing light feeds back visual information for the performance to continue as specified (referred to as Repetitive mode where the sensor LED 73Q flashes at each GDM).

Laser Light Beam Projector 37 emits a flash beam simultaneous with detecting sensor 73L upon the determination that the sequence is complete by comparing specified number of GDM to detected GDM.

Laser Light Beam Projector 37 emits a flash beam simultaneous with detecting sensor 73R upon the determination that the sequence is complete by comparing specified number of GDM to detected GDM.

Also sensors 73R and 77R having detected movement during the interval coincident to the beats in a musical phrase, is synchronous with a light cue emitted from an interval Lamp 35 at the musical phrase's beginning and end.

Also sensors 73L and 77L having detected movement during the interval coincident to the beats in a musical phrase, is synchronous with a light cue emitted from an interval Lamp 35 at the musical phrase's beginning and end.

Treadmill

Simultaneously with a beat, the user synchronizes GDM of lower extremities on a Foot platform of a treadmill in a series of lunges. The exercise methods comprise a motor skill set of four GDMs. The pattern of weight shift in stride (walking) compares to the inventive subject matter of lunging as follows: in gait there are two steps in each stride, a total of two GDMs to pace the body forward; in a modification of stride, i.e. The lunge, there are four movements that pace the body forward. At the start point in the first position GDM both feet meet with the Foot platform parallel to each other. The first GDM resembles a giant step executed by shifting weight toward the front of the treadmill to achieve the lunge. In the second GDM, body weight is evenly shifted between the legs, knees bent in tandem. The third GDM, ascending, is activated by shifting weight from the rear leg to the front foot for propulsion of the rear foot to make the leg come forward. In the fourth GDM the leg swings forward so the rear foot can make contact with the Foot platform.

To achieve lunging on a treadmill in the order whereby the sensors 73R, 73L, 73R, 73L detect a pattern, an LED flashes a light cue and feeds back visual information for the performance to continue as specified (referred to as Repetitive mode where the sensor LED 73Q flashes at each GDM).

Laser Light Beam Projector 37 emits simultaneous with detecting sensor 73L upon the determination that the sequence is complete by comparing specified number of GDM to detected GDM.

Also sensors 73R and 73 L having detected movement during the interval coincident to the beats in a musical phrase, is synchronous with a light cue emitted from an interval Lamp 35 at the musical phrase's beginning and end.

To achieve lunging on a treadmill in the order whereby the sensors 73L, 73R, 73L, 73R detect a pattern, an LED flashes a light cue and feeds back visual information for the performance to continue as specified (referred to as Repetitive mode where the sensor LED 73Q flashes at each GDM).

Laser Light Beam Projector 37 emits simultaneous with detecting sensor 73R upon the determination that the sequence is complete by comparing specified number of GDM to detected GDM.

Also sensors 73L and 73R having detected movement during the interval coincident to the beats in a musical phrase, is synchronous with a light cue emitted from an interval Lamp 35 at the musical phrase's beginning and end.

As noted above, the Laser Light Beam Projector 39 (controlled by Laser Light Beam Control Engine 770) may be used to project an image of one or more lines of demarcation 637. The lines of demarcation may be of different colors and may appear stationary with respect to the machine base or moving at the speed of the belt. These lines are meant to increase the precision of the user's spatial orientation when performing GDMs on a treadmill.

In the embodiments described herein, the audio signal (aka file) that is played back (at step 360) while the user performs a GDM sequence is a musical phrase. The phrase "audio file" is not intended to limit this description to specific modes of audio playback, but, rather, is used as a an alternative for audio signal. A musical phrase is a unit of musical meter that has a complete musical sense of its own, built from figures, motifs, and cells and combining to form melodies, periods and larger sections. A musical phrase is often equated to the length in which a singer or instrumentalist can play in one breath or, by some, as the smallest musical unit that conveys a more or less complete musical thought. Phrases vary in length and are terminated at a point of full or partial repose, which is called a cadence. Use of a musical phrase instead of larger musical structures is advantageous for new users because it is simpler to synch GDM with shorter compositions. Experienced users may be able to perform to more lengthy music structures, but doing so may require using a variety of GDM sequences. Thus, the ability to playback discrete musical phrases as the audio signal is an important aspect of the invention.

Using a single musical phrase as an audio signal to be played back requires detailed data concerning the beat events in the selected musical phrase. Such information could be obtained for selected musical phrases and stored either locally 130 or in network storage 55 accessible through the internet or cloud. However when beat event data files are not readily available, a beat detecting (extracting) engine 730 may be used to obtain beat event data for selected music files. The beat detecting engine 730 executes beat detectors against stored music files. Beat detectors execute against the music inputs from the PCM (musical phrase), identifying the beat event locations. Groupings of sound signals from the files stream as beat messages from the PCM. A beat message consists of a period time and a distance to the next beat event, both expressed in units of seconds. Beat messages output values from this detector source into bpm (beats per minute) and in this case, the number of beats in the musical phrase. The data provides the content for the Audible pulses (APs) at the beat events that are to coincide with movements on and with the Foot platform(s). In other words if during a performance the number of movements of and on the Foot platform(s) is coincident with the number of APs, movement will be judged to be at locations of the beat events (BE) in the music.

Figure 7:
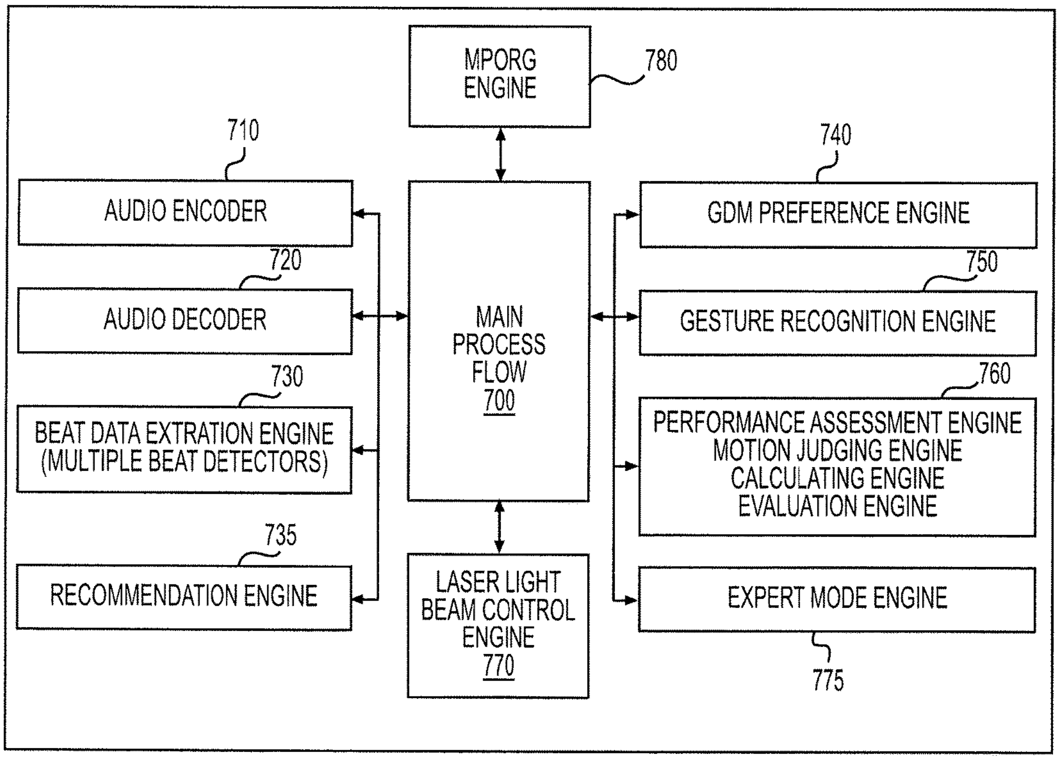
FIG. 7 is an overview of exemplary software architecture in an embodiment of the invention.

The CPU 100 preferably runs a motion judging engine (MJE) to judge whether the number of movements of the Foot platform (GDM performance) coincides with the number of Audible Pulses. As shown in FIG. 7, the motion judging engine may be part of the Performance Assessment Engine 760. The motion judging engine monitors (scans) all detection signals corresponding to the number of data positions related to beat events and movement of the Foot platform based on the detecting states of the sensors. Specifically the MJE monitors the number of movements and the variables noting their pattern: for example monitors how the sensors 73R, 77R, 73L, 77L enter their detecting states at a location of a beat event in patterns exemplifying movement made from left to right or movement from right to left i.e., 73R, 73L, 73R detecting simultaneous to 77R, 77L, 77R and then during the next musical phrase, 73L, 2L, 73L detecting simultaneous to 77L, 77R, 77L (or vice versa). In other words if a performance is in a pattern corresponding to the Audible pulses derived from the sound information (music inputs) and the sensors enter their detection states according to the pattern, the number of movements on and with the Foot platform is judged to correspond to the number of BE in the musical phrase.

A calculating engine calculates the number of correspondences (ratio) between the content information at the beat events (APs) and the detections. As shown in FIG. 7, the calculating engine may be part of the Performance Assessment Engine 760.

Before a GDM performance, data input from the music file is identified by the beat detecting engine (BDE). In a GDM performance the sensors 73R, 73L, output light cues and the CPU tabulates the detections. A difference is calculated from the number of music inputs reflected in the data (Beat Events) and the number of sensor signals detected (movements on and with the Foot platform). The new value represents the ratio of beats to movements—an equal value reflecting a perfect score where by the number of detections is relative the number of AP stimuli. Evaluations are made by enumerating a sum value of detections by a left sensor, and a sum value of detections by a right sensor. The sums of relative detection signals and the sums of beat events are also used to evaluate results presented in a score.

An evaluating engine includes a score calculator. As shown in FIG. 7, the Evaluation Engine may be part of the Performance Assessment Engine 760. The score calculator gives a cumulative of the detections made relative to the assessment of user preferences for GDM. The pattern in which the sensors 73R and 73L make their detections at the BE provides further content for evaluation. A maximum of two detections, preferably by a same sensor, for the first and last beats of the musical phrase, result from user preferences for Interval cuing. The detections that follow are then made in the same manner by the sensor opposite. In other words if a performance originates with a right sensor detecting on the first beat, the performance originating with a left sensor detecting on the first beat will be considered the next performance.

In Interval cuing GDM performances will be evaluated as a correct movement pattern with a given number of cues per musical phrase resulting in standard value of 2. A sum may be derived from the number of beats in a musical phrase multiplied by the number of repeated musical phrases relative to the total number of detections. All sums may be presented as score information.

In the method of repetitive cuing, the pattern of detection relies on the motion sensors entering their states coincident with BE. In addition to the interval cues (Lamp 35) emitted at the beginning and end of the musical phrase, GDMs cause the sensors flash light (LED) and in addition to the detections received in response to the standard number of cues emitted by the Lamp 35. These additional detections increase the sum total of all detections. Results presented in repetitive cuing as score info may be derived from the number BE in the musical phrase, multiplied by the number of musical phrases repeated and the number of detections made.

GDM identified by an opposite sensor flagged as left or right dominant will be evaluated as a correct movement pattern. A GDM that is complete is assessed to contain the same number of GDM preferences in which case the light cue of a flash beam coincides with the cessation of movement at the end of the musical phrase and if the GDMs are coincident with the number of beats in the musical phrase the a same sensor detection may be made at the first and last beat of the phrase and will be also synchronous with the interval lamp cues provided by the system.

The results displayed and stored (at step 370) may include a score according instructed by the user preferences as follows:

- the beats in the musical phrase, the beats in the musical phrase multiplied by the number of musical phrases repeated
- the sum of right detections, the sum of left detections, the sum total of detections relative to the preferences for number of GDM sequences and the number GDMs in each sequence
- the beats in the musical phrase, the beats in the musical phrase multiplied by the number of musical phrases repeated and the ratio of detections in Repetitive cuing mode,
- the beats in the musical phrase multiplied by the number of musical phrases repeated and the ratio of detections in Interval cuing mode, (the total number of beat events×standard cues 2)

FIG. 7 is an overview of exemplary software architecture in an embodiment of the invention. The software controlling the main processes may be run in the CPU 100 or in special purpose microprocessors such as the Audio Processor 150 or Gesture Recognition Processor 139. As shown, the software includes the Main Process Flow 700, which is generally shown in FIG. 3. The software also includes an Audio Encoder 710, an Audio Decoder 720, a Beat Data Extraction Engine 730 (which may optionally include multiple beat detectors), a Recommendation Engine 735 for suggesting audio or GDM based on user performance, a GDM Preference Engine 740, Gesture recognition Engine 750, a Performance Assessment Engine 760, a Laser Light Beam Control Engine 770, Expert Mode Engine 775 and a MPORG Engine for coordinating functions related to multi-player online role playing gaming through the network 50. The Performance Assessment Engine 760 may include subroutine for Motion Judging, Calculation and Evaluation. A separate engine may also be provided for processing foot pedal motion (step 390) and foot pressure signals. Naturally the functions performed in engines 710-780 could be incorporated into main process flow, but use of separate engines permits adaptation of commercially available solutions for functionality that is ancillary to the core functionality of the present invention. To the extent the specific processes for achieving specified functionality are not described here, there are commercially available solutions available such as audio encoders and decoders, for example.

Figure 8:
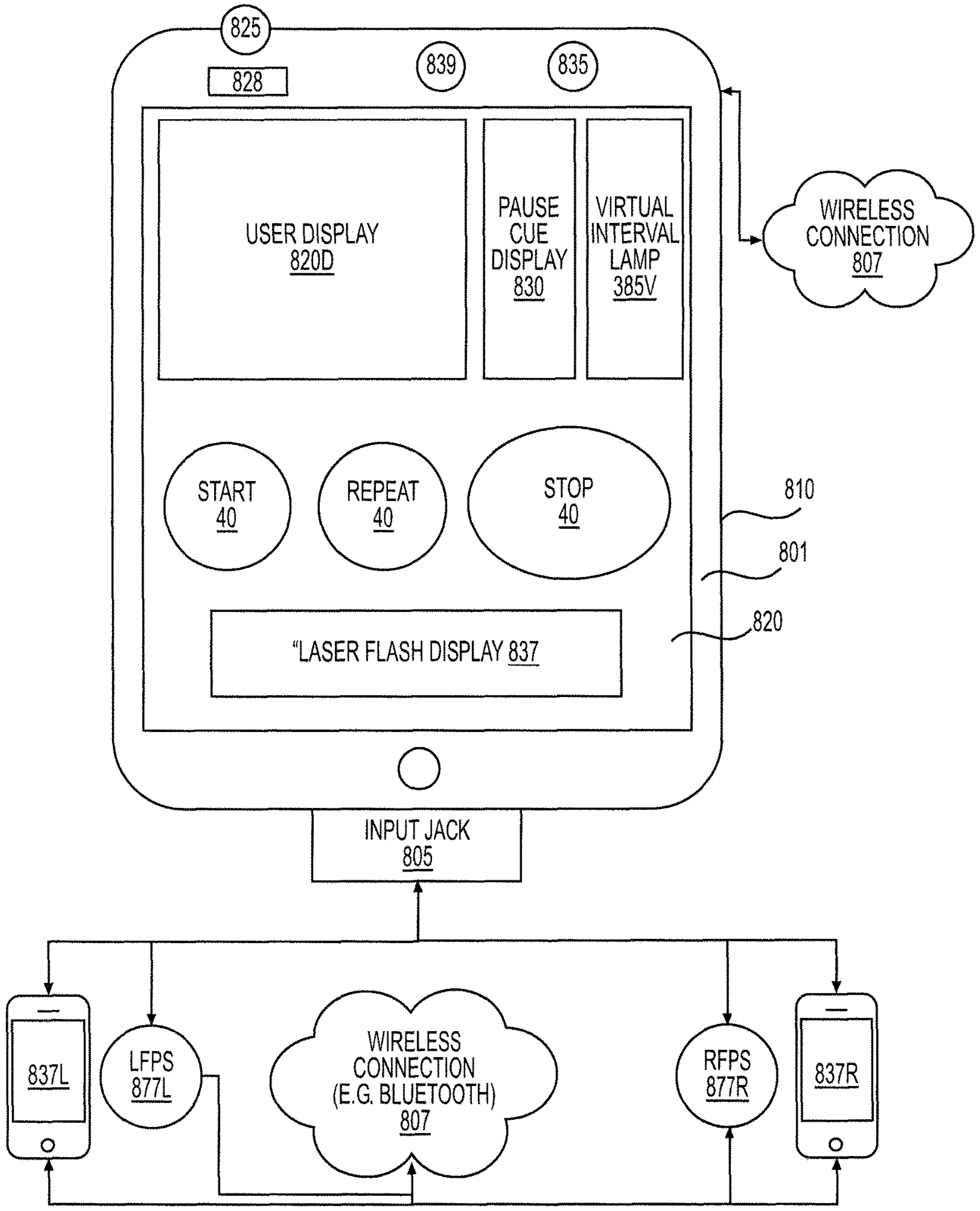
FIG. 8 is a schematic view of a general purpose multipoint touchscreen computing device adapted for use in the invention.
Figure 8A:
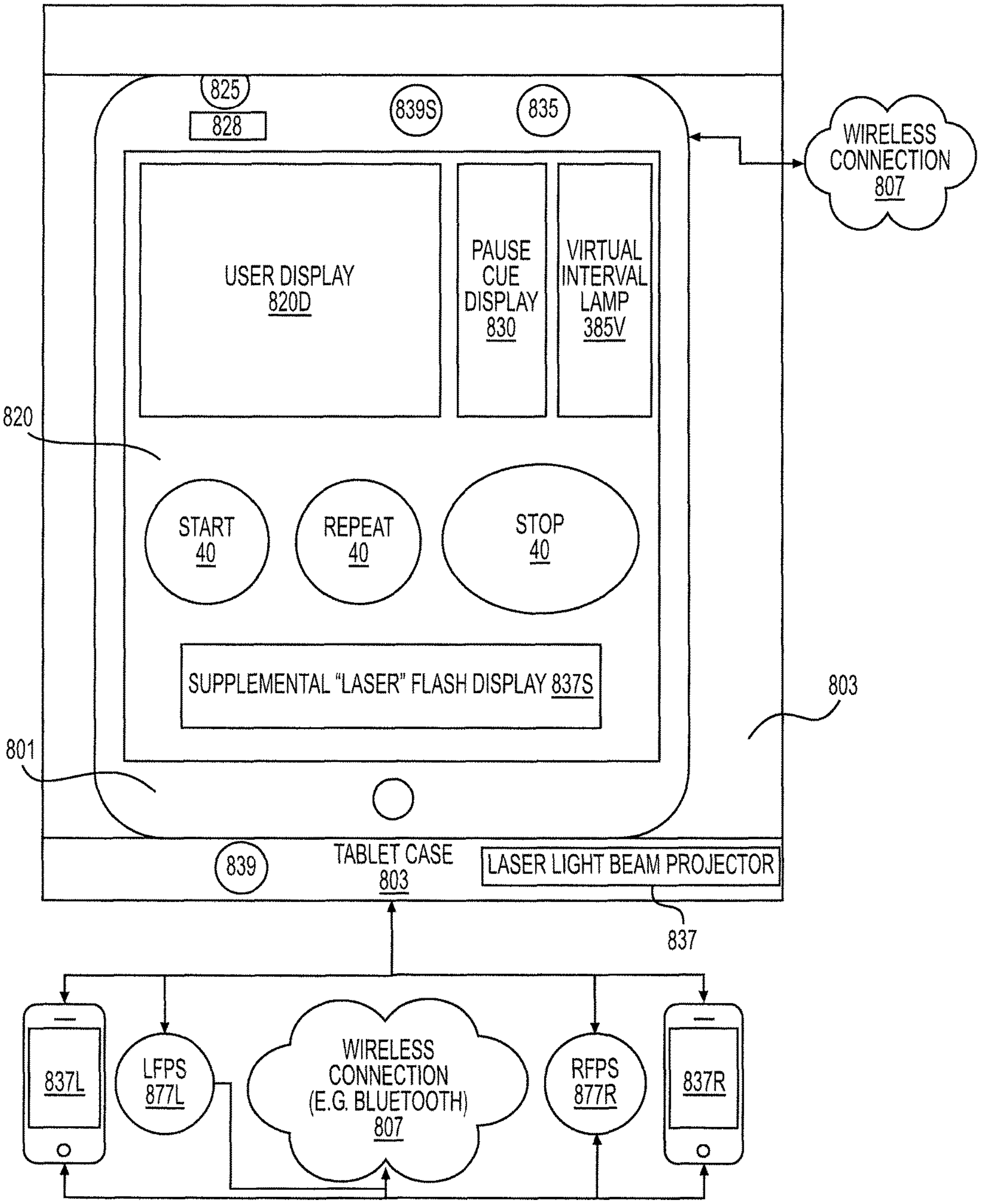
FIG. 8A is a schematic view of a general purpose multipoint touchscreen computing device with a casing providing additional hardware adapted for use in the invention.

As evident from the foregoing description, much of the functionality of the invention may be computer implemented. Thus, while the exemplary embodiments described above in connection with FIGS. 4-6 show a special purpose Control Panel 10 connected to the cardio fitness machine and associated hardware attached to portions of the cardio fitness machine, it is possible to implement the invention using more portable equipment. As shown in FIGS. 8 and 8A, for example, the invention may be implemented using a general purpose tablet computer or "smart phone" together with sensors that may be connected wirelessly (or wired) to the general purpose touch screen computing/communication device (tablet or smart phone).

As shown in FIG. 8, the general purpose computing/communication device 810 includes a casing 801 housing internal components and a multi touch screen 820 that covers most of the face of the device 810. The touch screen 80 is the primary user interface for operating the device. General purpose touch screen computers typically include components analogous to most of the components of the Control Panel described and shown in FIG. 2 (with the CPU being an acceptable substitute 100 for special purpose processors such as 139 and 150). Such devices use application software to cause the computer to perform tasks (applications) beyond the running of the computer itself. Such software is called software application, application or most commonly just an "app." The hardware in the typical device 810 is capable of executing an app directing the process flow of FIG. 3 and the other software engines shown in FIG. 7. Thus, the general purpose device of 810 could be used to run a app embodiment of the invention.

In the embodiment shown in FIG. 8, the hardware features found on the general purpose device are used to the extent possible. Thus, the audio jack 825 and speaker 828 are used as a substitute for the audio jack 25 and speaker 28 described above. A camera 839 may be used for some form of time of flight sensing (though a dedicated time of flight sensor and camera 839 in FIG. 8A is preferred) as an alternative to the camera 39 described above. The camera flash 835 may be used as alternative to the interval lamp 35 (or a virtual Interval lamp 835*v* could be displayed on the touch screen 820). The touch screen 820 could be used to display other components including the user display 820*d*; the pause cue display 830; a virtual "laser" flash display 837 and user selection buttons 40. The motion sensors 837L, 837R and pressure sensors 877L, 877R could be wirelessly connected to the device 810 through a wireless connection 807 or a wired connection using an input jack 805. The motion sensors 837L, 837R are detachable mountable to a surface of the cardio fitness machine. The pressure sensors 877L, 877R could be detachable mounted the cardio fitness machine as well, but it may be preferable to locate the sensors in a user's shoe. Motion sensors could also be attached to (Sewn into) user's apparel or bands worn by the user.

As described above, an embodiment of the invention may be implemented in a general purpose tablet or smartphone. Depending on the specific device, however, the available hardware may be sub-optimal. Where desired a special purpose protective case 803 may be used to both protect the device 810 and provide supplemental hardware to facilitate the present invention.

As shown in FIG. 8A, the device 801 is the same as described above in connection with FIG. 8. In this embodiment, however, the device 801 is encased in a separate case 803 that has, at least, a laser light beam projector 837 and a time of flight sensor and camera 839 built into the case 803. The components 837, 839 in the case are connected to the device 801 to provide enhanced hardware functionality that is closer to that found in the Control Panel 10 described above. The case 803 may also include one or more input jacks to allow the motion and pressure sensors to be connected by wire (as an alternative to the wireless connection 807). Other hardware components such as lamps, selection buttons and speakers can be provided in the case 803 as desired.

The present invention results in surprising improvements in exercise efficiency. The precise reasons for this synergistic increase is not yet certain, but it is believed that the present invention facilitates an exercise method that engages physiologically complex brain processes to shape and modulate brain and behavior and systems and methods for facilitating the method. Researchers have demonstrated that rhythm creates anticipation and predictability. Rhythm organizes time and rhythmic events are referenced and synchronized against underlying sensations of pulse patterns—pulses establish anticipation and predictability (audio beats are examples of pulse markings). The primary element in music that creates the perception of time is rhythm. Rhythm may enhance brain operations by providing structure and anticipation in time. Indeed, rhythm may be central to optimizing basic learning and perception processes. Motor response may be synchronized to an auditory rhythm and responding slightly ahead of time—within conscious perception of coincidence turns the task into a feed forward response.

Research suggests that music can uniquely engage the brain as a language of time, providing temporal structure to enhance learning and perception, especially in the areas of cognition, language and motor learning. Auditory rhythm is a powerful sensory cue that can regulate motor timing and coordination.

Rhythmic entrainment is linked to feed forward response. In the auditory mode, synchronization is an anticipatory response to an event that has not taken place, but whose precise occurrence time is known. Auditory rhythm can entrain the rhythmic motor responses—considering the nature of rhythm as a temporally predictable structure of timed events, responding ahead of the beat makes sense simply by maximizing the benefit of anticipation to programming the motor responses. As a result of the equidistant beat sequence, it is known to the brain when the beats will occur. Responding slightly ahead of time turns the task into a feed forward response a few milliseconds after the beat occurred, which provides feedback at a time when no correction of the response interval is possible. Receiving the beat feedback after the executed response gives appropriate sensory confirmation when corrections can be made for the next response cycle. Research suggests the existence of a central nervous system timing mechanism that helps regulate and control motor behavior. Support is found in the fact that humans are able to synchronize movement with external rhythmic sources as in clapping and dancing to music. Once synchrony of tapping to a metronome beat has been attained, the rate of tapping can be maintained after the metronomes stimulus has been removed. If we assume this mechanism has a role in controlling cyclic movement that is not driven by an external rhythm, we may expect that the consistency/variability of the timing of target contact will be a function of the precision of this internal timing system.

Visual cues are not as effective as auditory cues based on comparisons of visual cues and with auditory metronome cues possibly because rhythm accesses a central motor control system that, unlike visual cues, operates independently from peripheral mediators. Rhythmic activities inspire spontaneous growth of new neural circuits in the brain, improving physiological functions such as motor execution, and cognitive functions including memory and learning. The brain has several different rhythms known as Alpha, Beta, Delta and Theta waves, and there are also oscillating waves between the two hemispheres. As we age the rate of these hemispheric oscillation decreases and sometimes some parts of the brain develop abnormal or low oscillation rate, which can result in movement impairment or progressive cognitive deficit. The brain is equipped with music-specific neural networks, while auditory cues processed in the brain differently for language and music with some overlapping regions especially when singing or listening to the lyrics on the music. The brain has distinctive features of neural systems supporting music and language while separating phonological phrases (combined with melody) that are processed as music bilaterally, from semantic sentences (processed as language) that occur more in the left hemisphere. Monotonic rhythmic cues, such as finger tapping or listening to the metronome has a bilateral effect on brain activation similar to variable rhythmic cues like listening or dancing to music, but unlike the general effect of music, monotone cues create specific associations with areas that support activities such as movements and cognitive functions. Bilateral brain activation with monotonic auditory cues has been documented to inspire spontaneous brain reorganization that can support improvement in movements and cognitive functions.

Accordingly, the invention facilitates rhythmic entrainment to achieve surprising improvements in the efficiency and effectiveness of exercise through rhythmic exercise. The present invention provides an exercise method engaging physiologically complex brain processes to shape and modulate brain and behavior and systems and methods for facilitating the method. The method preferably comprises a sequence of goal directed movements GDM (exercise routine) that is synchronized to rhythmic cues in a feed forward fashion that allows the user to anticipate the cues (feed forward) and optimize (smooth, make more precise and efficient) the entire range of exercise motion. As used in this context, "optimize" means "an optimal balance of expenditure of energy (cost) and useful motion (benefit) to achieve the most efficient and enjoyable exercise." Naturally, "optimize" is used in the real world context to suggest an improved cost/benefit balance that represents an improvement that can approach theoretical optimization. As used in this application, "Exercise" is the movement of joints to challenge muscles in different ways. An "Exercise Routine" is the topography of movement of joints designed to be repeated to maximize safety and muscle strength gains, i.e., the repeated movement of joints in a specific sequence, patterns and/or range to challenge muscles in different ways. In the context of this application, a GDM sequence could be considered a precision exercise routine. The complete sequence patterns and/or range of movement that is repeated may be referred to as a "rep" or repetition. Performing the joint movements at the intended pace and in the intended sequence, pattern and/or range of movement is referred to as "precise movement," "exercise precision" and "precise form." "Exercise precision" is essential to optimal and efficient exercise. Failure to use precise form during a training set can result in injury or an inability to meet training goals—since the desired muscle group is not challenged sufficiently. The word "exemplary" is used herein to mean "serving as an example, instance, or illustration." Any aspect described herein as "exemplary" is not necessarily to be construed as preferred or advantageous over other aspects.

As described, the invention provides a method, system and equipment to facilitate goal directed movement. Through use of the method, system and equipment, the user will experience an enhanced GDM with improved results and increased efficiency. In accordance with another important aspect of the present invention, the improved user experience creates business opportunities that can benefit the user, the system provider and vendors—especially as users become more accustomed to use of the invention and advance to more sophisticated audio signals and/or GDM sequences.

In particular, the method, system and equipment of the present invention are designed to motivate the user to identify and make available information about themselves including music preferences and demographic information that could include physical attributes (age, gender, height, weight), and geographic location. In addition, the method, system and equipment can capture the user's performance pattern, efficiency and preferences. Moreover, the method, system and equipment can be designed such that the user is encouraged to experience sensory impressions (such as viewing images on a screen) for much of the duration of the GDM session. By collecting and processing all of this available information it is possible to achieve utility that cannot be otherwise achieved.

It is possible to provide add on's such as games, reward systems (real or virtual) or feedback/exercise history sites on the internet that will encourage a user to register and thus provide even more demographic information.

By way of example only, using the method, system and equipment of the invention in communication with other users through the internet or other networks or clouds, it is possible to:

Compare a user's performance to other similar users.

Compare a user's performance with musical phrases, melodies or songs of one "demographic type" to performance with songs of another "demographic type" and make suggests as to the best type of music for THAT user [demographic type as used here means the beat rate and/or other statistics of the music that can be compared].

Identify music that the user is most likely to perform well to, based on the users performance when using different types of music and an analysis of the "demographics" of music the user has used in the past.

Allow the user to purchase music [musical phrases, melodies or songs].

Identify advertising demographics of the user based on musical preferences, demographic information provided by the user (to use the equipment or register for a "add ons" offered on the web—using any or all of the available information, it is possible to display advertising sensory impressions to the user throughout the GDM session—for example, visual impressions on a display screen or audio impressions. Because the user is a content, but "captive" audience for an extended period and because of the insight into the particular user that can be obtained from all information collected about the user (especially musical preference, which is something not often coupled with the other types of information collected, it is possible to target advertising very accurately.

In this sense, the method, system and equipment of the invention make it possible to bring together knowledge of a user's musical preferences (which is indicative of certain user traits) with other information that is available to enhance advertising.

Other embodiments of the invention are naturally possible the wide range of available equipment for sensing applied pressure and motion. The sensors 37, 77, 837, 877 and time of flight sensors may be designed and arranged to detect motion in a sensing area include the range to the left and right above the users waist.

The system of the invention may also be operated in an EXPERT mode. The EXPERT mode may be coordinated using an Expert Mode Engine 775 that repurposes system components so that, in EXPERT mode, the audio signal is played and the system records the user's GDM as detected by the sensor system and stores the recorded sequence as a new GDM. In this way a preferred GDM sequence may be associated with an audio signal. This EXPERT mode allows an experienced user to easily create GDM sequences for a variety of musical phrases or other audio signals. The EXPERT mode could also be used by a less experienced user to store the GDM sequence the "created" in connection with a favorite musical phrase or other audio signal. The system can assess the new GDM sequence using the performance assessment engine 760, for example. A new GDM sequence for a particular musical phrase or audio signal that is created using the EXPERT mode may be stored (locally 130 or on network storage 55) and made available for use by others, if desired. It may be desirable to identify (and perhaps limit storage for use by others only to) those GDM sequences having a comparatively high performance assessment, i.e., GDM sequences that are appropriately synched to the audio signal. Using the EXPERT mode, users (especially experienced users) could create an eco-system of user created GDM sequences associated with a wide variety of music. Such new offerings could be sold or otherwise made available to improve the user experience.

Although the detection of the movement patterns herein described are presently novel these and other movement patterns known to the inventor may be embodied in other forms of technology as CPU input i.e. as coordinates in software data that may be used as stored detection information in addition to the sound information so that a user may follow a pattern more precisely whereby light emissions for all known patterns to the inventor display instructively to the user for reproduction of said patterns according to musical phrases and songs known to the user.

Although the detection of movement is herein described to be used in conjunction with audible stimuli, visual stimuli acquired in the instance of the above description of patterns known to the inventor becoming realized as coordinates and may be included as challenging to the user. User performances may be compared to more advanced performances for scoring in an MultiPlayer Online Role Playing Game [MPORG] where participants choose avatars to represent, for example, their physical attributes and earn points to change their physiques by performing the exercise first and uploading their own coordinates afterward to achieve a more enhanced physical attribute Players can buy such attributes but it should be costly to play. If this functionality is desired a conventional MPORG engine 780 may be used to control system functionality and interface with the network 50.

As noted above, the sensor system of the invention may include sensors embedded (or otherwise attached to) footwear, apparel and other athletic wear (anything worn by the user). In this context, the use of apparel specific to the promotion of enhanced methodology may be included in the motion sensor system and method of rhythmic cuing. Footwear and athletic wear that embodies the present invention whereby the sensors are embedded within the apparel that enable detections to be made and seen as visible cues further expanding the possibilities for make and use.

When cardio fitness equipment includes or is used with virtual or augmented reality equipment sensory cues as described herein may be integrated with the virtual/augmented reality experience. For example, visual cues may be provided with the virtual or augmented reality that the machine user is experiencing. The visual cues could be lines of demarcation or foot or hand "targets" associated with goal directed movements. Visual, audio and other sensory feedback could be provided within the virtual/augmented reality experience. To these ends, the equipment could include a headset 950 in electronic communication (via data cable 948 or wireless) with the control panel 10 and a virtual reality module (within control panel 10) for generating the sensory images and cues to provide a virtual augmented reality experience. The headset is worn on a user's head and configured to integrate with the control panel. The headset may include sensors (biosensors, position sensors) and at least one display screen in front of the user's eyes. An optical subassembly interposed between the display screen and the users eyes provides position adjustment or splitting or the image to achieve an immersive effect. The headset 950 is shown connected the stationary exercise cycle 900, but it should be appreciated that the headset 950 may be connected to the control panel 10 of any of any cardio fitness machine by a data cable 948 or wirelessly.

Virtual or augmented reality may be provided though image and sensory projections controlled by the control panel. For example, lines of demarcation projected onto the equipment. A more immersive implementation according to this invention, is a virtual reality (VR) headset 950 secured to a user's head sufficiently to permit goal directed exercise movement. Known VR headsets (e.g., Oculus Rift and PlayStation VR) are often referred to as head mounted displays, but a more secure attachment is provided to accommodate exercise type movement. The hardware can create a life size, 3D virtual environment without the boundaries associated with TV or computer screens. Video is sent from the control panel to the headset wirelessly or via a cable (e.g., HDMI) or a smartphone slotted into the headset. VR headsets use either two feeds sent to one display or two LCD displays, one per eye. The headset includes goggles 955 with adjustment 956 to match the distance between eyes, which varies from person to person. Lenses in the goggles 955 focus and reshape the picture for each eye and create a stereoscopic 3D image by angling the two 2D images to mimic how each of our two eyes views the world ever-so-slightly differently. Head tracking in the VR headset 955 (e.g., 6DoF (six degrees of freedom)) plots a user's head movement in terms of your x, y and z axis to measure head movements forward and backwards, side to side and shoulder to shoulder, otherwise known as pitch, yaw and roll. Various internal components w can be used in a head-tracking system such as a gyroscope, accelerometer and a magnetometer (typically provided by MEM's chips). LEDs 954 arranged around the headset provide 360 degree head tracking with an external time of camera monitoring these signals Headphones 952 increase the sense of immersion. The motion sensors and time of flight sensors described herein enhance the virtual or augmented reality experience. The helmet 955 may further include biosensors at interior locations (generally indicated at 958) to allow collection of neuroactivity data from users.

The system could support sales of music (musical phrases and other audio signals), custom GDM sequences and other tools to facilitate use of the invention. A motion sensor system and method of rhythmic cuing may allow the user to purchase music identified as suitable of certain user traits, with other information that is available to promote information sharing with other domains outside of the proprietary domain such as health care networks, agencies and all those dedicated to public interests. In particular, the particular motion patterns and rhythm of a user—detected through use of the invention—can be used to create a GDM profile for that user. Based on the GDM profile (stored locally 130, on network storage 55 or on a memory card 23 or wireless tag such as a RFID chip, for example) the system may recommend music and/or GDM sequences for the user. The processing for this recommendation engine 735 could be performed in the CPU or in a separate recommendation engine processor. Diverse musical phrases like a juke box, categorized according to the beats in the musical phrase (and possibly recommendation) may be presented for sale and/or use to the user through the control panel 10, 810.

Positron emission tomography (PET) brain imaging (or other imaging techniques) could be used to determine the extent to which (and provide evidence that) neuronal arousal with precision execution of motion increases with a rhythmically cued activity, evidencing that plasticity is made possible in brain tissue, in addition to growth in muscle tissue. PET brain imaging may enhance the evidence with before and after results and offer more to the fields of study in audio sound processing in humans and neurology.

Improvements in beat detection will make it more practical to offer more options for a listener to base his impressions on including note onsets, drumbeats and patterns, and harmonic changes. To this end, a plurality of beat detectors may be launched simultaneously (in beat detection engine 730, for example) to improve the overall accuracy and experience of a system and method of the present invention. A plurality of monitors aggregating information from multiple detectors generates a more advanced beat tracking response over an individual detector operating independently. This improvement in digitizing music will benefit usage of the present invention and the ability to achieve the objective of performing goal directed movements in response rhythmic cuing.

One form of a GDM sequence begins with the upper body extending a hand toward 71 L or 71R and retracting it. A user's arms can be raised so that the elbow joints are level with the shoulder joints and by bending each arm at the elbow the hands become level with the face and in close proximity of the user's eyes. In this case the upper limbs can be located in 3D space relating to a familiar type of upper body exercise i.e., bicep curl, shoulder press, tricep extension etc. With one arm extended, the other is in a stop location. The extension and retraction may be performed in a series whereby at commencement of a musical phrase both arms are in the start location and beginning and ending positions of extension and retraction are monitored independently by 71R and 71L in addition to 73R and 73L.

Sensing movement of the limbs can facilitate additional forms of exercise so that while standing on a treadmill the user may extend and retract a left lower limb independently of a right lower limb and the upper limbs may enter their detection states similarly and simultaneously with the lower limbs, however while performing right side movements and left side movements on an exercise bike, the lower limbs are constrained to the path of motion provided by the pedals. As such pressure applied to the 70R, 70L, is indicative of method described in 0085 thru 0094 pertaining to the elliptical cardio fitness machine except that the user is seated instead of standing upright.

In a seated position stopping of pedaling is considered aversive during exercise on a stationary bicycle. However, as the user applies force to the pedals, 70R AND 70L, the unique structure of a spin exercise bicycle permits for standing upright. Starting and stopping locations may be established with the system flagging initiation of a GDM sequence with pressure sensors 77R and 77L entering their detection state according to the method where for example 77R was detected before 77L indicating the user resumed a standing position by pressing more on the left pedal (77L) after being seated from a GDM sequence that began by pressing harder with right pedal (77R). The start location would then be recognized by the system flagging the beginning position, either 77R or 77L, entering its detection state according to a right side movement or a left side movement upon playback of the musical phrase selected.

In order to implement Starting and stopping locations with the pedals of a stationary spin type exercise bike, a user selection according to the method is as follows: body weight is supported with both hands on the handle bar (pressure sensors 77L, 77R provided at convenient locations or sleeve mounted pressure sensors that can be at location that is adjustable to user preference) and with one foot on one pedal, 70R or 70L, the knee is flexed and the hip is raised, the other foot is bearing down (foot pedal pressure sensors 77R or 77L is activated accordingly) on the other pedal, 70R or 70L, leg is strait, knee is fully extended, the hip is lowered. This being the start position, a user applies enough pressure to force one pedal, 70R or 70L, half way up to the next position and the other pedal 70R or 70L, down to a next position, and then returns it back to the start position (or position from which it has departed), which according to the method is also NOW the end position or a completed GDM sequence When a user is seated on a stationary bike the customary placement of user's hands is on the handle bar. As such a pressure sensor 77L, 77R may be placed on the handle bar. The system would monitor the lower limbs as discussed but in this case and the upper right limb would enter the exercise space associated with 73R and the upper left limb would enter the exercise space associated with 71R so that 70R, 73R and 71R would all enter their detection states simultaneously with at least the first and last beat of a musical phrase.

The user would perform this movement sequence, several times in a row, or would switch sides, or legs so to speak, bearing down on the other pedal and beginning the process with the other side of the body with detections being made by 70L, 73L, 71L and handle bar pressure sensors 77L, 77R. By removing a hand from the handle bar, the upper limb enters into the exercise space associated with either the sensor 73R or 73L in a movement sequence known as a row or possibly a tricep extension, completing the sequence when both hands are on the handle bar. The sequence following can then begin on the opposite side with the system monitoring the absence of pressure on the handle bar and the sensors entering their detection states to indicate a right initiated goal directed movement sequence or a left initiated goal directed movement sequence.

Monitoring the pulsing of the infrared light measures would be compared to the measure of beat pulses so that the positions of a movement sequence would be identified by the system according to the user's selection of a start location and an end location of a sequence of right and left side movements so that motion contrast indicative of the beginning position of a sequence (Right side) can be identified as the inverse in the previous starting location of the former sequence (left side) and also by identification of the present sequence's stopping location (right side). Images of the sequences and distortions between sequences are recognized as deviations between start and stop locations for right side movements and left side movements and further where the onset and completion of audio files may suffice to indicate begin and end positions relative to the series of right side movements and left side movements in ongoing sequences of this nature performed to music or more specifically, according to a beginning position and to an end position relative to the onset and completion of a musical phrase with at least 3 beats.

The continuous effort of meeting the challenge of besting inverse movement patterns that user's synchronize with musical phrases can uniquely activate a pseudo competition between the right and left side of the body. As a result the aural and proprioceptive learning modalities that reciprocally advance this entrainment skill set minimize the need for the visual cues (including the visual pause cue feature of the control panel). Similar to performances of the centuries old exercise format of Tai-chi, the acts of repetition become ingrained and succeed in reforming neural connectivity in all areas of executive function-memory, language (in this instance relating to musical structure), motor skills, concentration, judgement.

Neuro-technology is capable of measuring intensity of focus and workload, which is compatible with the proposed rhythmic objective of using a foot platform to increase entertainment benefit during exercise In addition to these biometrics may be the monitoring of connectivity in the brain during rhythmic exercise if an algorithm was implemented to measure how the left hemisphere is firing when performing right side movements and how the right hemisphere is firing while performing left side movements. The crossover between hemispheres may account for the sensation of a contest where the left hemisphere of a right dominant person becomes aware of the right hemispheres competing for attention.

As described herein, the system and equipment is useful in facilitating movement that keeps time with music. Such synchrony helps the body use energy more efficiently. When moving rhythmically to a beat, the body does not have to make as many adjustments to coordinate movements as it would without regular external cues. In some exercise, users moving in time to music require less oxygen to do the same work as users who did not synchronize their movements with music. Rhythmic movement helps maintain a steady pace, reduce false steps, and decrease energy expenditure.

To facilitate this entrainment benefit further with a spatio-temporal dynamic, a model for monitoring motor patterns that correspond with the order of beat events in a musical phrase (commonly known as a Loop) may be used. By way of example, sequential movement input derived from foot placement in a known common spatial area of a foot platform in a method for acquiring spatio-temporal behaviors during exercise on a cardio-fitness machine will be described. FIGS. 2A-2D, contextualize the method for increasing efficiency of a cardio fitness machine through entertainment of the limbs. These illustrations of motor patterns that can be made with the lower limbs facilitate improved exercise by favoring movement using the non-dominant side of the body. Though depicted in the context of a staircase, performances of these patterns pertain to cardio fitness machines whereby the upper limbs as well as the lower limbs engage in the proposed method of rhythmic exercise. As such performances requiring inverse patterning become rhythmically entrained and novel ambidextrous efforts in the upper and lower limbs may be monitored.

Generally speaking, in the presence of music, auditory-motor coupling is responsible for the bodily sensations associated with seemingly involuntary gestures of head nodding and foot tapping and the voluntary gesture of hand clapping. However, because musical sounds are communicated in a cohesive language, a component of a song may be used to increase awareness of what is perceptible spatially about music, in combination with what is perceptible temporally about music. Human perception of how much room is available to move either to produce sounds with an instrument or to mimic series of sounds with movement is explored within motor therapies as well as Musicology. Neurological Music Therapy (NMT), Embodied Music Cognition (EMC), Transactional Gesture Analysis (TGA), Bio-Kinetic Resonance Theory (BKRT) and the phenomena of "musical chunking" and the "home position" may be shown as criteria to assess how movement, constrained to foot platforms during time spent exercising, may elicit motor sensory skills to further entrain.

The musical phrase is a predominant feature of musical language. Within the structure of a song, the musical phrase possess' a repetitive characteristic. Similar to language phrases, a musical phrase is sequentially organized—regularly has an important loci of its organization—its beginning and its end; the organization often relates the beginning to the end, and often involves the reappearance at the end of something that occurred at the beginning. Active listening may therefore evoke recognition of this characteristic most purposefully when positions of the body arrive at an intended spatial location that corresponds with the origin or conclusion of a musical phrase. For example in line dancing, salsa, the hokey pokey or the Macarena, all movement performances are segmented and patterned to coincide with a repetitive component of the song. The quality of human detection of music events can be telling of decisions made ahead of time in order to perform segmented motor patterns that cycle repetitively. This may be explained as the phenomenon of musical chunking whereby people segment the sounds in order to decide what are the sonic events and what are the gestures that match these events. The ability to successfully execute motor patterns repetitively without the use of visual prompts gives reason to speculate that rhythmic movement is achieved prospectively as a result of decisions made predominantly with the auditory domain. An outcome of listening to segments of audio stimuli that are familiarly orderly may combine with segments of motor patterns to provide an objective for acting prospectively in exercise regimes that combine with music.

Making decisions prospectively in motor activities that are inclusive of music is currently unavailable to users in systems that generate audio stimuli using system latency for future movement input; or in others where the pattern of movement is unknown, and visual prompts are generated to compel movement input; or in others that require real time mimicking of movement for input as in video game systems. Even when these systems have music playing, the objective is to focus the user's attention on viewing, not listening. Because musical entrainment of sensory skills occurs in the auditory-motor pathways, positioning of the body in a substantially known spatial area corresponding to a user's right movement, or left movement, in combination with musical features, may improve upon current systems and methods for movement input. Audio-goal directed decisions that result in rhythmic modifications to gait while using foot platforms of cardio-fitness machines may introduce the novelty of listening for beat events for the purpose of learning starting and stopping locations for sequential input of movement procedures instead of following visual prompts.

A model for monitoring motor patterns together with a Loop (musical phrase) to further entrainment benefit with a spatio-temporal dynamic is illustrated in FIG. 3. As described, the system and equipment allows monitoring of a user's motor pattern to correspond with a procedural programming language in the series of computational steps in FIG. 3 and provides a method for acquiring spatio-temporal behaviors during exercise on a cardio-fitness machine. The order of beat events in the Loop may be monitored together with the sequence of an audio goal directed movement pattern. The green lines indicate that input derived from the starting and stopping locations for foot placement correspond to the beginning and ending positions of a right side movement and the beginning and ending positions of a left side movement and to the audio file playback of a Loop.

In the model shown in FIG. 3, there is an objective placement of limbs from which the exercise movement departs (begins) and to which it returns (ends). This position can be referred to as a home position. The criteria for position, timing, and location of movement procedures requires consideration of both the periodicity of movement and the objective of error free movement.

Prospective decisions of where to position a movement is as crucial as when to position a movement. Periodicity is perceivable in the absence of sound between beat pulses. Beats are represented in wave forms. The distance between wave peaks is measured in Hz, which occurs at a rate or frequency of one per second. When listening to music and planting one foot down at a time the body is capable of registering a respective rate of movement. Bio-Kinetic Resonance Theory (BKRT) says that a tempo of 120 beats per minute is typical of top selling songs because bi-pedal motion similarly resonates a 2 Hz pulse in the body. Occupying an amount of space is relative to keeping the rate of movement consistent with the periodicity of sounds or with the absence between sounds. If we consider the minute silence between sounds to represent the formation of reflexive time expectations, it becomes evident that organizing movement also entails an ordered inertia. It follows that perceptions of when to make a movement correlate with how long to wait before moving; which should be equally inclusive of deciding where; in which case the decision may entail moving slowly and too far out of a tight range or moving quicker within a roomier range. Continuous adjustment in rhythmic timing can be understood counterintuitively to include foresight of time lags together with spatial constraints to keep the rate of movement consistent and thereby error free.

Successful coupling of auditory-motor skills is evident in activities that rely upon periodicity to make movement segments consecutively. Movement correction and its importance to the continuity of movement segments is fundamental to the activity of skipping rope. Juggling is an example of an activity that requires continuous repetitive movement segments requiring consistency in maintaining sequences of error free movement. Spatio-temporal behaviors can be learned and mastered with repeated practice similar to way people learn to juggle or use a jump rope. One may have success as it is said by getting the hang of it, but all movements take up a certain amount of time, and merging with this time, provide for its measurement; a sense of rhythm depends on units of time derived from movement written into them. Rhythmic movement is best viewed as the result of a time ordered objective, and one of complexity.

FIGS. 2A-2D illustrates motor patterns derived from a sequence of audio-goal directed movements with a home position while using a foot platform to exercise to music. Cardio-fitness machine's employ foot platforms that meet with compliance for measurements associated with gait. Foot platforms of escalators, staircases, and cardio-fitness machines all offer familiar and substantially known spatial areas for achieving gait. Everyday use of a staircase does not evoke timing or spatial limitations as necessary to the method of climbing a stairs but upon contemplation of climbing two stairs at a time, and breaking the rule of start/stop locations for foot placement, use of the staircase presents an opportunity for experimenting with alternative stride methods and/or gait modifications; as is also the case where an injury to a lower extremity forces the task of climbing stairs one at a time. In this instance a start and stop location is met on each stair step. In keeping with the prospective decisions that must occur in each of these scenarios, and being that gait occurs by positioning one foot after the other, the lead foot initiating a motor pattern would be of importance to the succession of foot placements. If a time ordered objective for spatio-temporal directed movement were to entail switching the lead foot from stair step to stair step, we would have reason to speculate that initiating right side movements and left side movements in inverse patterns in combination with the recognition of starting and stopping locations may be similar to exploration of timing and location of trajectories in spatio-temporal behaviors of entrainment study in musicological experiments.

FIGS. 2A-D show how a rhythmic objective may provide a strategy to reduce errors and remain organized during monitoring of rhythmic input with minimal visual cues. This method of maintaining consistency of home position in sequences of audio-goal directed movements brings new meaning to the combination of music and exercise. The enhancement of audio-motor coupling skills resulting from prospective decisions for spatial deployment inclusive of temporal inertia in addition to temporal resonance in the body during exercise to music provides the basis for the conception of audio interface wherein visual stimuli becomes superfluous. By minimizing error and staying in motion, the novelty of rhythmically organized chunking of movement and data can now be understood as a spatio-temporal behavior formulated from the continuous repetition of motor patterns that are regulated through the auditory motor pathways where recurring musical segments provide tracking opportunities for monitoring continuity of movement input within the known and common spatial boundaries of foot platforms of a cardio-fitness machine.

Figure 2A:
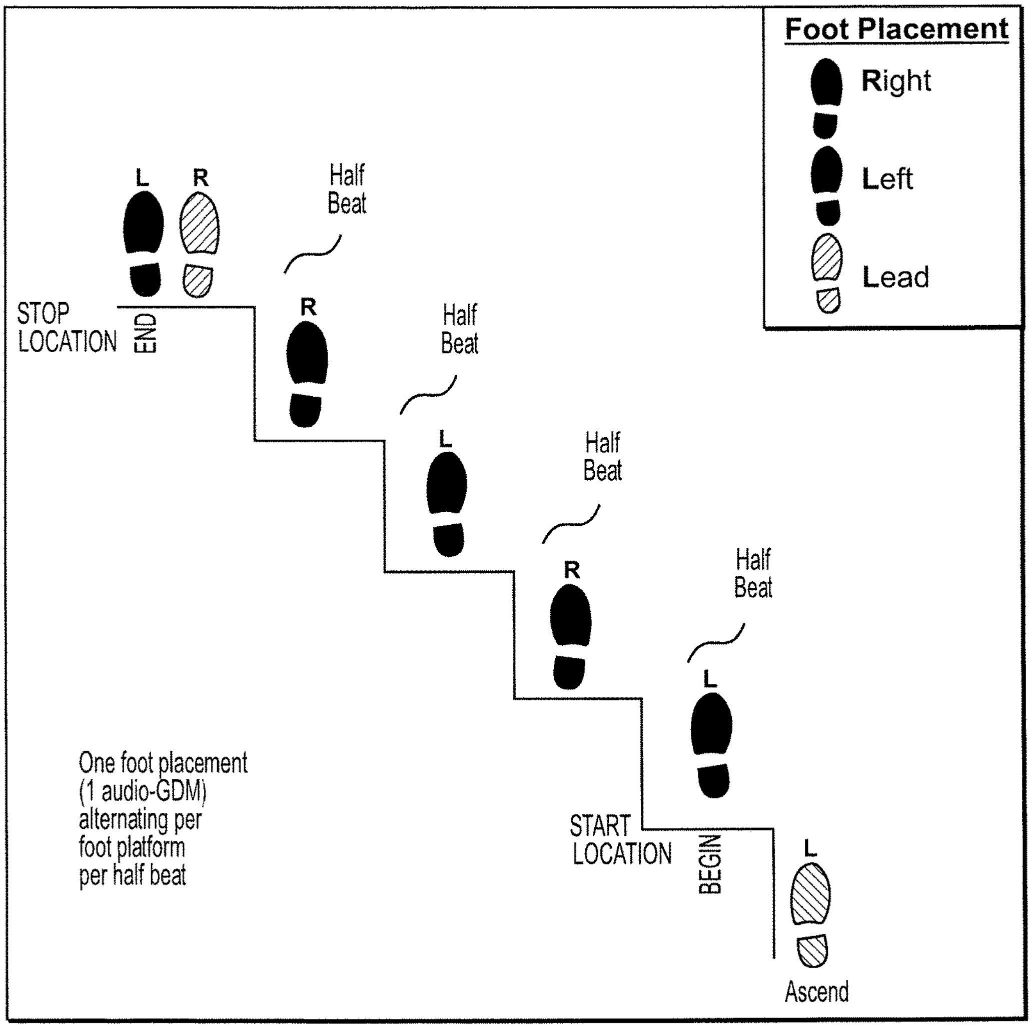
FIG. 2A illustrates a motor pattern of left dominant audio-goal directed movements in a sequence.

Using foot placement on the "foot platform" of a staircase as an example, FIG. 2A illustrates a motor pattern of left dominant audio-goal directed movements in a sequence:

In a substantially known spatial area of a foot platform corresponding to a right side movement and a left side movement, the begin position is initiated with an audio-goal directed movement to the starting location of an alternating foot platform on the left side.

In a substantially known spatial area of a foot platform corresponding to a right side movement and a left side movement, the end position is made in the stopping location with the same foot.

A motor pattern and sequence of audio-goal directed movements (audio-GDMs) in a substantially known spatial area of a foot platform corresponding to a right side movement and a left side movement simultaneously corresponding to the timing and organization of a beat event.

Figure 2B:
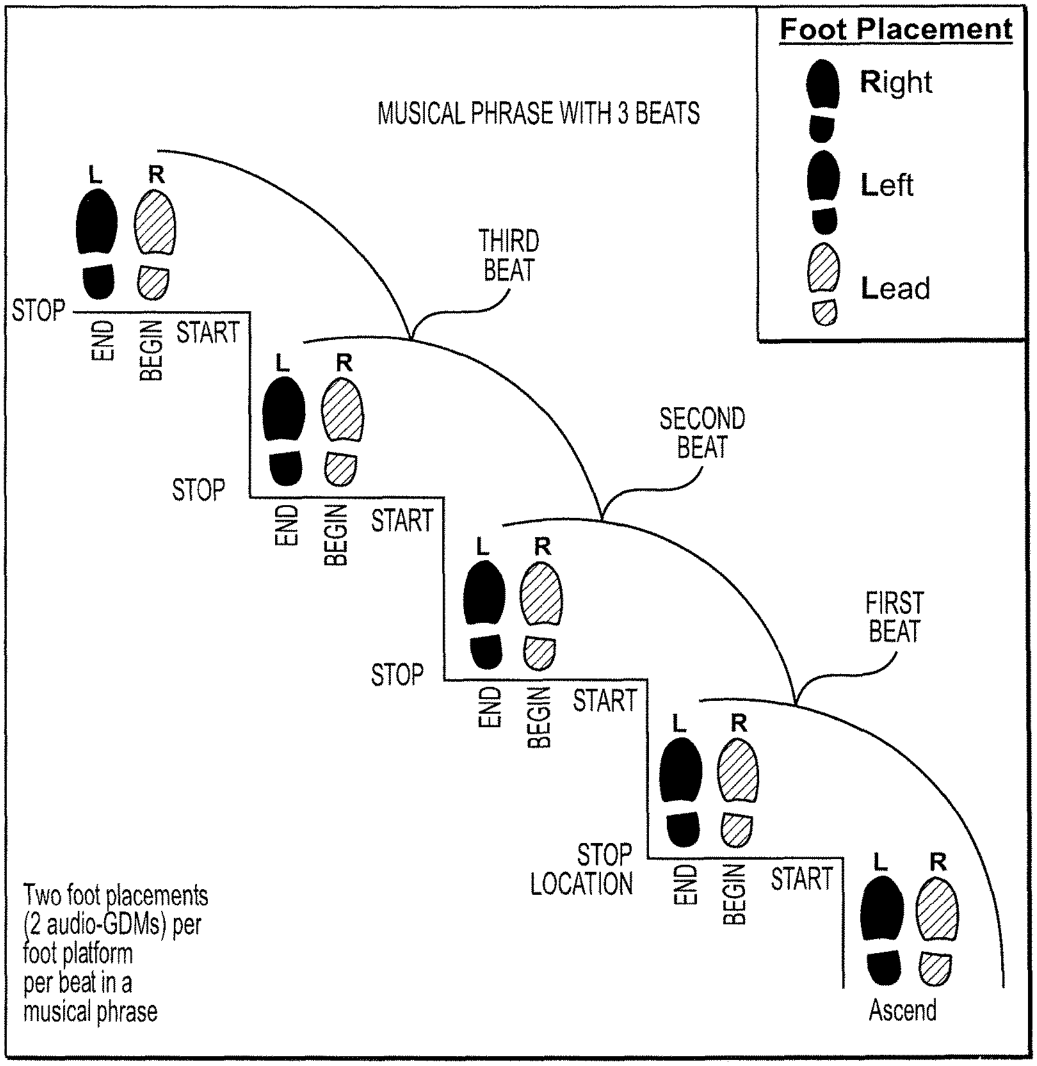
FIG. 2B illustrates a series of identical right dominant audio-goal directed movement sequences.

FIG. 2B illustrates a series of identical right dominant audio-goal directed movement sequences:

In each starting and stopping location in a substantially known spatial area of a foot platform corresponding to a right side movement and a left side movement, which is the same foot platform, the stopping location for a left foot audio-goal directed movement is in the end position.

In each starting and stopping location in a substantially known spatial area of a foot platform corresponding to a right side movement and a left side movement, which is the same foot platform, the begin position is initiated with an audio-goal directed movement to the alternating platform with the same lead foot.

An identical motor pattern of two foot placements (2audio-GDMs) per audio-goal directed movement sequence in a substantially known spatial area of a foot platform corresponding to a right side movement and a left side movement simultaneously corresponding to the timing and order of beat events in a musical phrase with 3 beats.

Figure 2C:
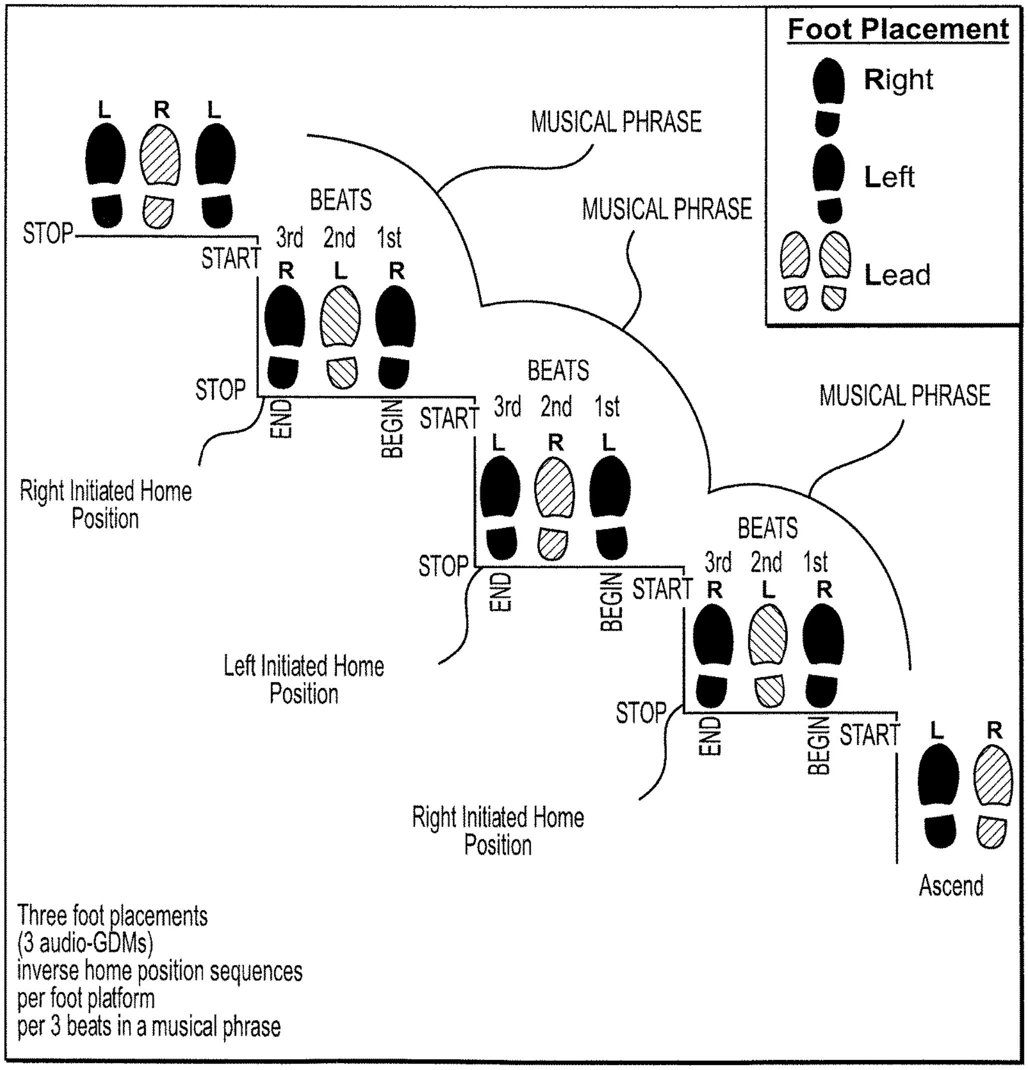
FIG. 2C illustrates a series of a home position motor pattern of inverse dominant audio-goal directed movement sequences.

FIG. 2C depicts a series of a home position motor patterns of inverse dominant audio-goal directed movement sequences:

In each starting location of a substantially known spatial area of a foot platform corresponding to a right side movement and a left side movement the beginning position is the inverse of the movement in the previous starting location and will be the same inverse movement in a subsequent starting location.

In each stopping location of a substantially known spatial area of a foot platform corresponding to a right side movement and a left side movement ending with a left side movement, a beginning position is initiated to the starting location of the alternate foot platform with a lead right side movement and vice versa.

A home position motor pattern of three foot placements (3 audio-GDMs) per audio-goal directed movement sequence in a substantially known spatial area of a foot platform corresponding to a right side movement and a left side movement ending on the same side the sequence began simultaneously corresponds to the timing and order of beat events in a musical phrase with at least 3 beats.

Figure 2D:
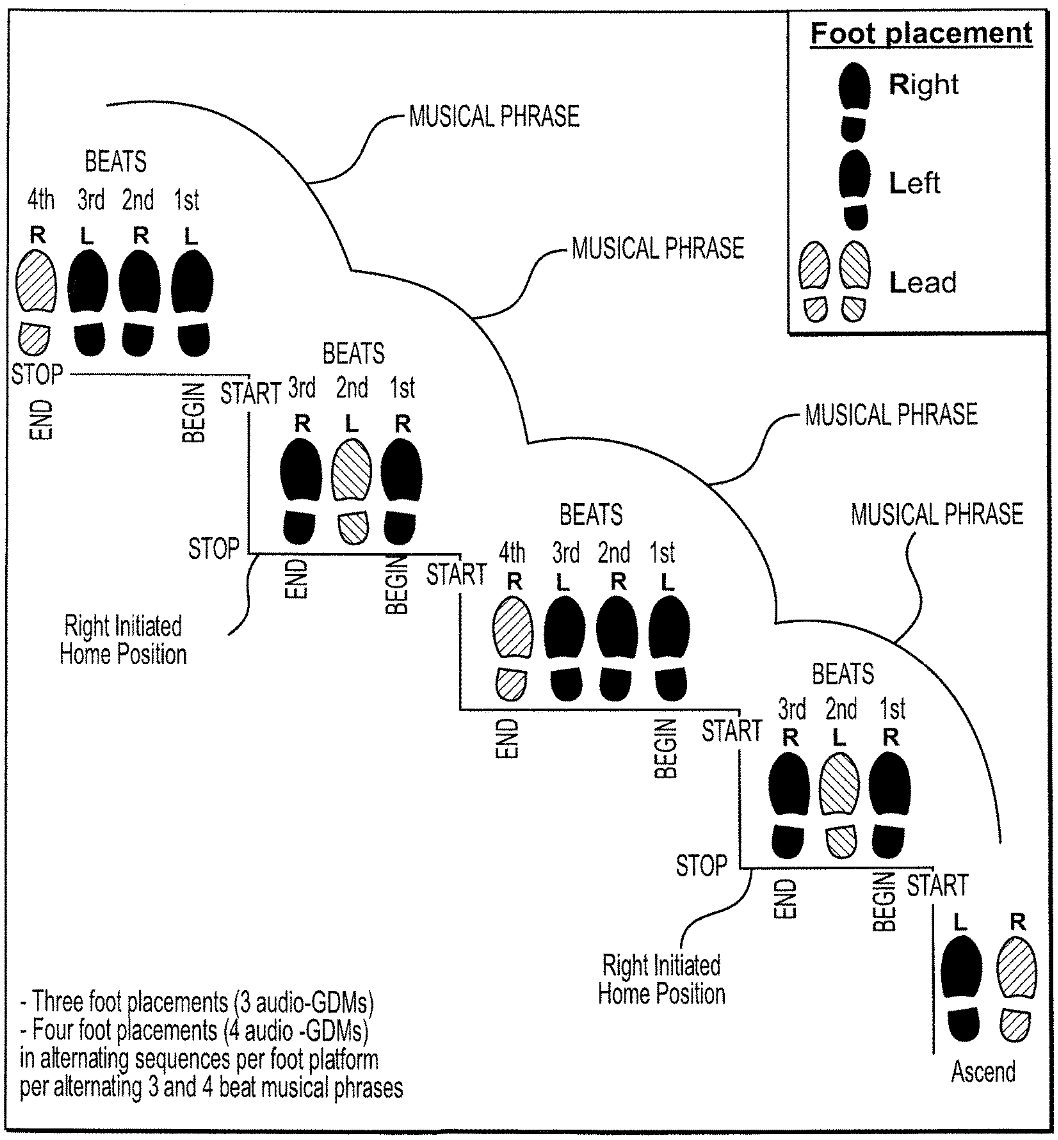
FIG. 2D illustrates an alternating series of home position motor patterns of inverse dominant movement sequences.

FIG. 2D depicts an alternating series of home position motor patterns of inverse dominant movement sequences:

In each starting location of a substantially known spatial area of a foot platform corresponding to a right side movement and a left side movement the beginning position is the inverse of the movement in the previous starting location and will be the same inverse movement in a subsequent starting location.

In each stopping location of a substantially known spatial area of a foot platform corresponding to a right side movement and a left side movement ending with a left side movement, a beginning position is initiated to the starting location of the alternate foot platform with a lead right side movement and vice versa.

Two alternating home position motor patterns of three and then four foot placements (3 audio-GDMs alternating with 4) per audio-goal directed movement sequence in a substantially known spatial area of a foot platform corresponding to a right side movement and a left side movement ending on the same side the sequence began simultaneously corresponds to the timing and order of beat events in a musical phrase having 3 beats alternating with another musical phrase having 4 beats.

In each starting location of a substantially known spatial area of a foot platform corresponding to a right side movement and a left side movement the beginning position is the inverse of the movement in the previous starting location and will be the same inverse movement in a subsequent starting location.

In each stopping location of a substantially known spatial area of a foot platform corresponding to a right side movement and a left side movement ending with a left side movement, a beginning position is initiated to the starting location of the alternate foot platform with a lead right side movement and vice versa.

Two alternating home position motor patterns of three and then four foot placements (3 audio-GDMs alternating with 4) per audio-goal directed movement sequence in a substantially known spatial area of a foot platform corresponding to a right side movement and a left side movement ending on the same side the sequence began simultaneously corresponds to the timing and order of beat events in a musical phrase having 3 beats alternating with another musical phrase having 4 beats.

Although it has become commonplace that people synchronize with a beat while pedaling for exercise, indoor cycling to music lacks a spatiotemporal dimension. Indoor cycling, as opposed to outdoor, requires no visual skills. If one is seated and using pedals with eyes closed the task is achievable. However there still remains an opportunity to use auditory skills to establish timing and locations that correspond to musical events. Within the category of cardio-fitness machines, the potential of the indoor cycle remains less obvious to the Spinning method user, and to musical exercise in general, to regulate movement spatially according to the reciprocal relationship between periodic movement and musical periods. Rotating the pedal of a bicycle is akin to the sensation of planting a foot on the ground, one after the other. Because cadence in indoor cycling to music has been shown to entrain this rhythmic exercise behavior, conceivably, pedaling activates a 2 Hz resonance.

When using an exercise bike, if pedaling to music can activate a 2 Hz resonance in the same way walking or running on a treadmill does, or as presented, in the act of climbing a stair case as in FIG. 2A, then cadence can be performed fundamentally and categorically differently according to FIG. 2B, FIG. 2C, and FIG. 2D. The information presented demonstrates how the home position birthed from cadence modifies synchronization skills. And if f the auditory-motor system modifies exercise synchronization skills while seated on an exercise bike, entrainment in exercise builds on this skill set, more consecutively, more rhythmically and ultimately more efficiently, if it has a spatio-temporal dynamic. Rhythmic exercise using foot platforms of cardio fitness machines is likely to evolve in light of the conclusions from musicologists that support the spatio-temporal dimension of entrainment and emerging common knowledge in favor of transposing that benefit to exercising to music. To embody such in technology that marries music and exercise would improve exercising on cardio-fitness machines.

The embodiments described herein are exemplary and not intended to be exhaustive of the applications of the systems and methods of the invention.

What is claimed is:

1. A cardio fitness machine that generates sensory cues to guide a user in performing goal directed movements (GDM) in a GDM sequence in coordination with rhythmic elements of an audio file, where the GDM sequence comprises a plurality of distinct GDMs including an initial GDM at initiation of the GDM sequence and a final GDM at completion of the GDM sequence and the audio file comprises at least one musical phrase that contains at least three beat pulses, the cardio fitness machine comprising:

a control panel configured to receive user selections including at least a user selection of an audio file comprising at least one musical phrase that contains at least three beat pulses and a user selection of a GDM sequence comprising a plurality of distinct GDMs; wherein the control panel includes memory for storing data including stored audio file data and stored GDM sequence data; the control panel is further configured to load stored audio file data in response to the user selection of the audio file and load stored GDM sequence data in response to the user selection of the GDM sequence; determine a timing and location of the beat pulses in the user selected audio file and identify the plurality of distinct GDMs including a sequence of right limb movements and left limb movements in the user selected GDM sequence; the control panel further comprising an audio processor configured to obtain beat information for the user selected audio file and playback the user selected audio file, the user selected audio file playback having an initiation and a conclusion;

at least one foot support portion, the at least one foot support portion supported on the cardio fitness machine and configured for continuous movement along a known path;

a sensor system, the sensor system comprising sensor devices positioned and configured to detect motion in specific zones of movement including a first zone of movement corresponding to an exercise space associated with a right side of the user and a second first zone of movement corresponding to an exercise space associated with a left side of the user, the sensor devices comprising a first sensor positioned and configured to detect only movements in the first exercise space associated with a right side of the user and a second sensor positioned and configured to detect only movements in the second exercise space associated with a left side of the user; wherein the sensor system configured to detect the right limb movements and the left limb movements of the user and distinguish between the detected right limb movements and the left limb movements, wherein the control panel is further configured to receive signals from the first and second sensors indicative of a sequence of detected movements in the exercise space associated with the right and left side of the user and compare the sequence of detected movements to the user selected GDM sequence; and a plurality of sensory cue generators controlled independently of one another and configured such that a first sensory cue generator generates a non-audio sensory cue at the initiation and conclusion of the user selected audio file playback and a second sensory cue generator generates a sensory cue at the initiation and conclusion of the user selected GDM sequence.

2. The cardio fitness machine of claim 1, wherein the control panel is configured to determine the timing and location of the beat pulses in the user selected audio file using the loaded stored audio file data.

3. The cardio fitness machine of claim 1, wherein the control panel is configured to determine the timing and location of the beat pulses in the user selected audio file using a beat detection engine configured to extract beat data from the user selected audio file.

4. The cardio fitness machine of claim 1, wherein the sensor system comprises a time of flight sensing system positioned and configured to detect user movements in specific zones of an exercise space associated with a user and distinguishing between movement associated with an exercise space associated with a right side of a user and movements in an exercise space associated with a left side of a user.

5. The cardio fitness machine of claim 1, further comprising a wireless communication processor configured to receive signals from a plurality of wireless sensors worn by the user to detect user movements in performing the user selected GDM sequence.

6. The cardio fitness machine of claim 1, wherein the control panel is configured to compare timing of the detected right limb movements and left limb movements with the determined timing of the beat pulses in the user selected audio file and provide feedback to the user.

7. The cardio fitness machine of claim 6, wherein comparing the timing of the detected right limb movements and left limb movements with the determined timing of the beat pulses in the user selected audio file comprises comparing a number of beat pulses in the user selected audio file to a number of the detected right limb and left limb movements of the user.

8. The cardio fitness machine of claim 1, further comprising a data recording system configured to record and store the right limb and left limb movements of the user as detected by the sensor system during the user selected audio file playback as a new GDM sequence.

9. The cardio fitness machine of claim 1, wherein the first sensor and the second sensor are motion sensors.

10. The cardio fitness machine of claim 1, wherein the at least one foot support portion comprises two foot support portions that are moveable relative to one another, wherein one of the two foot support portions support the right foot of the user and the other one of the two foot support portions support the left foot of the user, the two foot support portions each comprising at least one pressure sensor, each of the at least one pressure sensor is configured to detect a pressure applied by the right foot and the left foot of the user and provide signals that allow the sensor system to distinguish between the right foot pressure and the left foot pressure.

11. The cardio fitness machine of claim 1, wherein the control panel is further configured to provide a visible pause cue during a pause period prior to the user selected audio file playback and control the user selected audio file playback and the plurality of sensory cues such that when the pause period ends, a first beat in the user selected audio file becomes audible, which is synchronous with the non-audio sensory cue generated by the first cue generator at the initiation of the user selected audio file playback, and wherein upon completion of the user selected audio file playback, which is synchronous with the non-audio sensory cue generated by the first cue generator at the conclusion of the user selected audio file playback, the control panel determines, according to user preference stored instructions, whether to repeat the user selected audio file playback and, if so, a new pause period is initiated, and if not a GDM performance assessment procedure is initiated, during which, the control panel is configured to monitor the user's movements by receiving a limb movement signal, determining if the limb movement signal came from the first sensor or the second sensor, and determining whether the limb movement signal received is the first limb movement signal of the user selected GDM sequence and, if so, flagging the user selected GDM sequence according to whether the limb movement was the left limb movement or the right limb movement;

store separate counts of the left limb movements and the right limb movements and determine whether the user has completed performing the user selected GDM sequence by comparing the counts of the left limb movements and the right limb movements to a number of beats pulses in the user selected audio file; and wherein the second sensory cue generator generating the sensory cue at the conclusion of the user selected GDM sequence in response to determining that the user has completed performing the user selected GDM sequence.

12. The cardio fitness machine of claim 1, wherein the cardio fitness machine is a cycle and the at least one foot support portion comprises two moveable foot support platforms; the two moveable foot support platforms comprising pedals that are constrained to move in a circular path and offset 180° with respect to one another.

13. The cardio fitness machine of claim 1, wherein the cardio fitness machine is an elliptical trainer machine and the at least one foot support portion comprises two moveable foot support platforms; the two moveable foot support platforms are moveable with respect to one another.

14. The cardio fitness machine of claim 1, wherein the cardio fitness machine is an Adaptive Movement Trainer (AMT) machine and the at least one foot support portion comprises two moveable foot support platforms; the two moveable foot support platforms are moveable with respect to one another.

15. The cardio fitness machine of claim 1, further comprising a head-mounted devices that is worn on a user's head and configured to integrate with the control panel, the head-mounted device comprising sensors and at least one display screen in front of the user's eyes; and an optical subassembly interposed between the display screen and the users eyes.

16. A portable audio file playback and cue generating device for use in association with a cardio fitness exercise equipment having at least one foot support portion supported on the cardio fitness equipment and configured for continuous movement along a known path and a time of flight sensor system positioned and configured to detect user movements in specific zones of an exercise space associated with a user and distinguishing between movement associated with an exercise space associated with a right side of a user and movements in an exercise space associated with a left side of a user, wherein the portable audio file playback and cue generating device is configured to generate sensory cues to guide the user in performing a sequence of known goal directed movements (GDM) in a GDM sequence in coordination with rhythmic elements of the audio file where the GDM sequence comprises a plurality of distinct GDMs including an initial GDM at initiation of the GDM sequence and a final GDM at conclusion of the GDM sequence and the audio file comprises at least one musical phrase that contains at least three beat pulses, the portable audio file playback and cue generating device comprising:

a control panel configured to receive user selections including at least a user selection of an audio file comprising at least one musical phrase that contains at least three beat pulses and a user selection of a GDM sequence comprising a plurality of distinct GDMs to be performed on a cardio fitness exercise equipment; the control panel configured to determine a timing and location of beat pulses in the user selected audio file and identify the plurality of distinct GDMs including a sequence of left limb movements and right limb movements in the user selected GDM sequence; wherein the control panel is further configured to receive signals from the time of flight sensor system indicative of a sequence of detected movements in the exercise space associated with the right and left side of the user and compare the sequence of detected movements to the user selected GDM sequence; the control panel further comprising an audio processor configured to obtain beat information for the user selected audio file and playback the user selected audio file, the audio file playback having an initiation and a conclusion; and a plurality of sensory cue generators controlled independently of one another and configured such that a first sensory cue generator generates a non-audio cue at the initiation and conclusion of the user selected audio file playback and a second sensory cue generator generates a sensory cue at the initiation and conclusion of the user selected GDM sequence.

17. The portable audio file playback and cue generating device of claim 16, wherein the control panel is further configured to provide a visible pause cue during a pause period prior to the user selected audio file playback and control user selected audio file playback and the generation of sensory cues such that when the pause period ends, a first beat in the user selected audio file becomes audible, which is synchronous with the non-audio sensory cue generated by the first cue generator at the initiation of the user selected audio file playback and wherein upon completion of the user selected audio file playback, which is synchronous with the non-audio cue generated by the first cue generator at the conclusion of the user selected audio file playback, the control panel determines, according to user preference stored instructions, whether to repeat the user selected audio file playback and, if so, a new pause period is initiated; and if not a GDM performance assessment procedure is initiated during which the control panel is configured to monitor the user's movements by receiving a limb movement signal, determining if the limb movement signal came from the right sensor or the left sensor, and determining whether the limb movement signal received is the first limb movement signal of the user selected GDM sequence and, if so, flagging the user selected GDM sequence according to whether the limb movement was a left limb movement or right limb movement, store separate counts of the left limb movements and the right limb movements and determining whether the user has completed performing the user selected GDM sequence by comparing the counts of the left limb movements and the right limb movement to a number of beat pulses in the user selected audio file; and wherein the second sensory cue generator generating the sensory cue at the conclusion of the user selected GDM sequence in response to determining that the user has completed performing the user selected GDM sequence.

* * * * *